(12) United States Patent
Daly et al.

(10) Patent No.: US 10,588,940 B2
(45) Date of Patent: Mar. 17, 2020

(54) USE OF ANGIOPOIETINS IN PROMOTING BLOOD COAGULATION AND IN THE TREATMENT OF BLOOD COAGULATION DISORDERS

(71) Applicant: Regeneron Pharmaceuticals, Inc., Tarrytown, NY (US)

(72) Inventors: Christopher Daly, New York, NY (US); Samuel Davis, New York, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 15/773,498

(22) PCT Filed: Nov. 4, 2016

(86) PCT No.: PCT/US2016/060527
§ 371 (c)(1),
(2) Date: May 3, 2018

(87) PCT Pub. No.: WO2017/079556
PCT Pub. Date: May 11, 2017

(65) Prior Publication Data
US 2018/0318392 A1 Nov. 8, 2018

Related U.S. Application Data

(60) Provisional application No. 62/252,217, filed on Nov. 6, 2015.

(51) Int. Cl.
| | |
|---|---|
| *A61K 38/18* | (2006.01) |
| *C07K 14/515* | (2006.01) |
| *A61P 7/04* | (2006.01) |
| *G01N 33/86* | (2006.01) |

(52) U.S. Cl.
CPC ............ *A61K 38/1891* (2013.01); *A61P 7/04* (2018.01); *C07K 14/515* (2013.01); *G01N 33/86* (2013.01); *C07K 2319/30* (2013.01)

(58) Field of Classification Search
CPC .......................... A61K 38/1891; C07K 14/515
See application file for complete search history.

(56) References Cited

U.S. PATENT DOCUMENTS

| | | | | |
|---|---|---|---|---|
| 7,008,781 | B1 | 3/2006 | Davis et al. | |
| 7,691,366 | B2 | 4/2010 | Koh | |
| 9,592,271 | B2 * | 3/2017 | Purcell Ngambo | .... C07K 16/22 |
| 9,968,653 | B2 * | 5/2018 | Purcell Ngambo | .... A61K 31/49 |
| 2007/0036756 | A1 * | 2/2007 | Hamada | ............... C07K 14/515 424/93.2 |
| 2009/0220463 | A1 * | 9/2009 | Kim | ....................... A61K 38/06 424/93.7 |
| 2014/0348806 | A1 * | 11/2014 | Stewart | ................... A61K 35/12 424/93.21 |

FOREIGN PATENT DOCUMENTS

| | | |
|---|---|---|
| WO | 01/05825 A2 | 1/2001 |
| WO | 15/066426 A2 | 5/2015 |
| WO | 17/079556 A1 | 5/2017 |

OTHER PUBLICATIONS

Jerebtsova et al., Aug. 2015, Angiopoietin-1 prevents severe bleeding complications induced by heparin-like drugs and fibroblast growth factor-2 in mice, Am J Physiol Heart Circ Physiol, 309: H1314-H1325.*
Koh et al., 2002, Biomedical significance of endothelial cell specific growth factor, angiopoietin, Experimental and Molecular Medicine, 34(1): 1-11.*
Tsigkos et al., 2003, Angiopoietins in angiogenesis and beyond, Expert Opin Investig Drugs, 12(6): 933-941.*
Hilbert et al., 2015, The angiopoietin/TIE receptor system: Focusing its role for ischemia-reperfusion injury, Cytokine & Growth Factor Reviews, 26: 281-291.*
Augustin et al., 2009, Control of vascular morphogenesis and homeostasis through the angiopoietin-Tie system, Nature Reviews: Molecular Cell Biology, 10: 165-177.*
Thomas et al., 2009, The role of the Angiopoietins in vascular morphogenesis, Angiogenesis, 12: 125-137.*
Davis et al., 2003, Angiopoietins have distinct modular domains essential for receptor binding, dimerization and superclustering, Nature Structural Biology, 10(1): 38-44 and 146.*
Fagiani et al., 2013, Angiopoietins in angiogenesis, Cancer letters, 328: 18-26.*
Jerebtsova et al., 2015, Angiopoietin-1 prevents severe bleeding complications induced by heparin-like drugs and fibroblast growth factor-2 in mice, American Journal of Physiology Heart and Circulatory Physiology, 309(8): H1314-H1325.*
Anastasiou et al., "Thrombomodulin as a regulator of the anticoagulant pathway: implication in the development of thrombosis," Blood Coagulation & Fibrinolysis, vol. 23(No. 1):1-10, (2012), XP055342516.
Davis et al., "Angiopoietins Have Distinct Modular Domains Essential for Receptor Binding," Nature Structural Biology, Nature Publishing Group, NY, vol. 10(No. 1):38-44, (2003). ISSN: 1072-8368, DOI: 10.1038/NSB880.
WIPO Application No. PCT/US2016/060527, PCT International Preliminary Report on Patentability dated May 8, 2018.
WIPO Application No. PCT/US2016/060527, PCT International Search Report and Written Opinion of the International Searching Authority dated Mar. 2, 2017.
Wu et al., "Pharmacokinetics of Peptide-Fc Fusion Proteins," Journal of Pharmaceutical Sciences, vol. 103(No. 1):53-64, (2014). ISSN: 0022-3549, DOI: 10.1002/jps.23783.

* cited by examiner

*Primary Examiner* — Amber D Steele
(74) *Attorney, Agent, or Firm* — Schwabe, Williamson & Wyatt PC; Gabe Amodeo

(57) ABSTRACT

The present invention provides methods for promoting blood coagulation and/or treating blood coagulation disorders in a subject in need thereof. The methods of the present invention comprise administering to a subject in need thereof a therapeutically effective amount of a pharmaceutical composition comprising an angiopoietin protein or a modified angiopoietin protein molecule such as AngF1-Fc-F1 or AngF2-Fc-F2.

15 Claims, 6 Drawing Sheets

Specification includes a Sequence Listing.

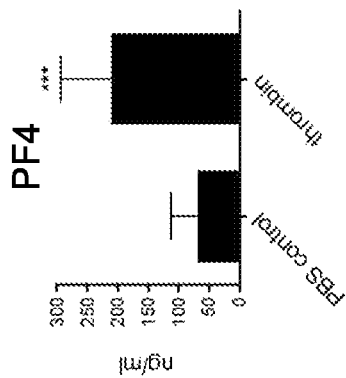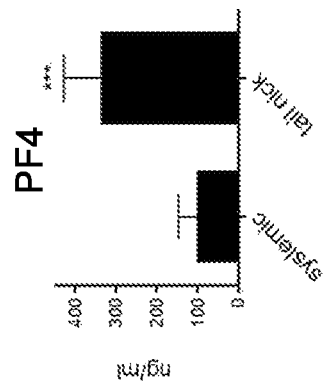
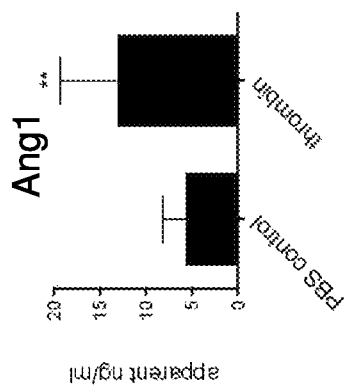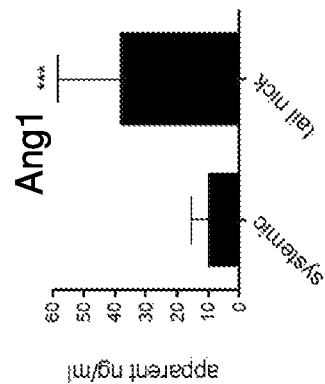
Fig. 5C
Fig. 5D

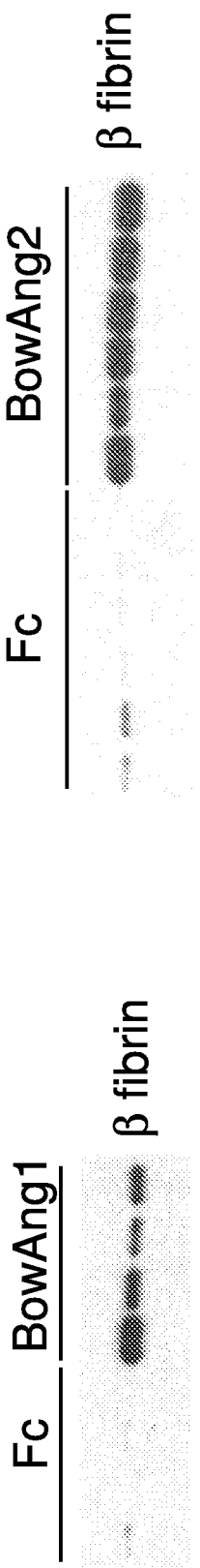
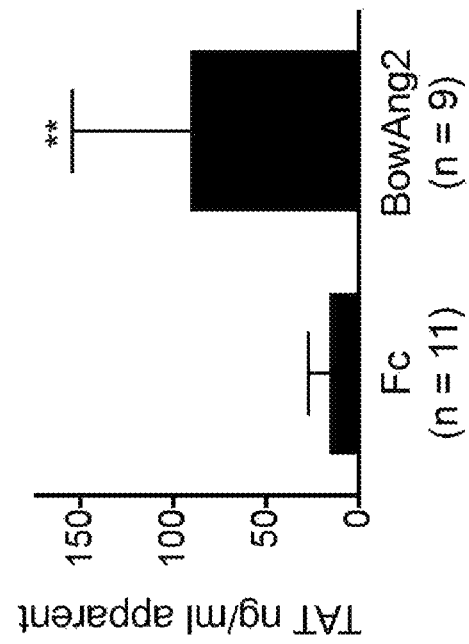
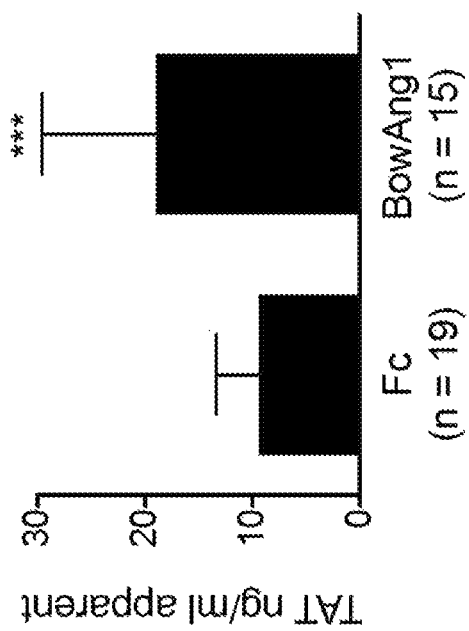
Fig. 6A
Fig. 6B

SEQUENCE LISTING

```
<160> NUMBER OF SEQ ID NOS: 9

<210> SEQ ID NO 1
<211> LENGTH: 1977
<212> TYPE: DNA
<213> ORGANISM: Artificial Sequence
<220> FEATURE:
<223> OTHER INFORMATION: Synthetic

<400> SEQUENCE: 1
ttcagagact gcgccgacgt gtaccaggcc ggcttcaaca agtccggcat ctacaccatc      60
tacatcaaca acatgcctga gcctaagaag gtgttctgca acatggacgt gaacggcggc     120
ggctggacag tgatccagca cagagaggac ggctccctgg acttccagag aggctggaag     180
gagtacaaga tgggcttcgg caacccttcc ggcgagtact ggctgggcaa cgagttcatc     240
ttcgccatca cctcccagag acagtacatg ctgagaatcg agctgatgga ctgggagggc     300
aacagagcct actcccagta cgacagattc cacatcggca acgagaagca gaactacaga     360
ctgtacctga agggccacac cggcaccgcc ggcaagcagt cctccctgat cctccacggc     420
gccgacttct ccaccaagga cgccgacaac gacaactgca tgtgcaagtg cgccctgatg     480
ctgaccggcg gctggtggtt cgacgcctgc ggcccttcca acctgaacgg catgttctac     540
accgccggcc agaaccacgg caagctgaac ggcatcaagt ggcactactt caaaggccct     600
tcctactccc tgaggtcgac caccatgatg atcagacctc tggacttcga caaaactcac     660
acatgcccac cgtgcccagc acctgaactc ctggggggac cgtcagtctt cctcttcccc     720
ccaaaaccca aggacaccct catgatctcc cggacccctg aggtcacatg cgtggtggtg     780
gacgtgagcc acgaagaccc tgaggtcaag ttcaactggt acgtggacgg cgtggaggtg     840
cataatgcca agacaaagcc gcgggaggag cagtacaaca gcacgtaccg tgtggtcagc     900
gtcctcaccg tcctgcacca ggactggctg aatggcaagg agtacaagtg caaggtctcc     960
```

```
aacaaagccc tcccagcccc catcgagaaa accatctcca aagccaaagg gcagccccga    1020
gaaccacagg tgtacaccct gcccccatcc cgggatgagc tgaccaagaa ccaggtcagc    1080
ctgacctgcc tggtcaaagg cttctatccc agcgacatcg ccgtggagtg ggagagcaat    1140
gggcagccgg agaacaacta caagaccacg cctcccgtgc tggactccga cggctccttc    1200
ttcctctata gcaagctcac cgtggacaag agcaggtggc agcagggaa cgtcttctca     1260 tgctccgtga tgcatgaggc tctgcacaac cactacacgc agaagagcct ctccctgtct    1320
ccgggtttta gagactgcgc agatgtatat caagctggtt ttaataaaag tggaatctac    1380
actatttata ttaataatat gccagaaccc aaaaaggtgt tttgcaatat ggatgtcaat    1440
gggggaggtt ggactgtaat acaacatcgt gaagatggaa gtctagattt ccaaagaggc    1500
tggaaggaat ataaaatggg ttttggaaat ccctccggtg aatattggct ggggaatgag    1560 tttattttg  ccattaccag tcagaggcag tacatgctaa gaattgagtt aatggactgg    1620
gaagggaacc gagcctattc acagtatgac agattccaca taggaaatga aaagcaaaac    1680
tataggttgt atttaaaagg tcacactggg acagcaggaa acagagcag cctgatctta     1740 cacggtgctg atttcagcac taaagatgct gataatgaca actgtatgtg caaatgtgcc    1800
ctcatgttaa caggaggatg gtggtttgat gcttgtggcc cctccaatct aaatggaatg    1860
ttctatactg cgggacaaaa ccatggaaaa ctgaatggga taaagtggca ctacttcaaa    1920
gggccaagtt actccttacg ttccacaact atgatgattc gacctttaga tttttaa       1977
```

<210> SEQ ID NO 2
<211> LENGTH: 658
<212> TYPE: PRT
<213> ORGANISM: Artificial Sequence
<220> FEATURE:
<223> OTHER INFORMATION: Synthetic

<400> SEQUENCE: 2

```
Phe Arg Asp Cys Ala Asp Val Tyr Gln Ala Gly Phe Asn Lys Ser Gly
1               5                   10                  15

Ile Tyr Thr Ile Tyr Ile Asn Asn Met Pro Glu Pro Lys Lys Val Phe
            20                  25                  30

Cys Asn Met Asp Val Asn Gly Gly Gly Trp Thr Val Ile Gln His Arg
        35                  40                  45

Glu Asp Gly Ser Leu Asp Phe Gln Arg Gly Trp Lys Glu Tyr Lys Met
    50                  55                  60

Gly Phe Gly Asn Pro Ser Gly Glu Tyr Trp Leu Gly Asn Glu Phe Ile
65                  70                  75                  80

Phe Ala Ile Thr Ser Gln Arg Gln Tyr Met Leu Arg Ile Glu Leu Met
                85                  90                  95

Asp Trp Glu Gly Asn Arg Ala Tyr Ser Gln Tyr Asp Arg Phe His Ile
            100                 105                 110

Gly Asn Glu Lys Gln Asn Tyr Arg Leu Tyr Leu Lys Gly His Thr Gly
        115                 120                 125

Thr Ala Gly Lys Gln Ser Ser Leu Ile Leu His Gly Ala Asp Phe Ser
    130                 135                 140

Thr Lys Asp Ala Asp Asn Asp Asn Cys Met Cys Lys Cys Ala Leu Met
145                 150                 155                 160

Leu Thr Gly Gly Trp Trp Phe Asp Ala Cys Gly Pro Ser Asn Leu Asn
                165                 170                 175

Gly Met Phe Tyr Thr Ala Gly Gln Asn His Gly Lys Leu Asn Gly Ile
```

```
            180                 185                 190
Lys Trp His Tyr Phe Lys Gly Pro Ser Tyr Ser Leu Arg Ser Thr Thr
            195                 200                 205
Met Met Ile Arg Pro Leu Asp Phe Asp Lys Thr His Thr Cys Pro Pro
            210                 215                 220
Cys Pro Ala Pro Glu Leu Leu Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser His Glu Asp Pro Glu Val Lys Phe Asn
            260                 265                 270
Trp Tyr Val Asp Gly Val Glu Val His Asn Ala Lys Thr Lys Pro Arg
            275                 280                 285
Glu Glu Gln Tyr Asn Ser Thr Tyr Arg Val Val Ser Val Leu Thr Val
            290                 295                 300
Leu His Gln Asp Trp Leu Asn Gly Lys Glu Tyr Lys Cys Lys Val Ser
305                 310                 315                 320
Asn Lys Ala Leu Pro Ala Pro Ile Glu Lys Thr Ile Ser Lys Ala Lys
                325                 330                 335
Gly Gln Pro Arg Glu Pro Gln Val Tyr Thr Leu Pro Pro Ser Arg Asp
            340                 345                 350
Glu Leu Thr Lys Asn Gln Val Ser Leu Thr Cys Leu Val Lys Gly Phe
            355                 360                 365
Tyr Pro Ser Asp Ile Ala Val Glu Trp Glu Ser Asn Gly Gln Pro Glu
            370                 375                 380
Asn Asn Tyr Lys Thr Thr Pro Pro Val Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly Phe Arg Asp Cys Ala Asp
            435                 440                 445
Val Tyr Gln Ala Gly Phe Asn Lys Ser Gly Ile Tyr Thr Ile Tyr Ile
            450                 455                 460
Asn Asn Met Pro Glu Pro Lys Lys Val Phe Cys Asn Met Asp Val Asn
465                 470                 475                 480
Gly Gly Gly Trp Thr Val Ile Gln His Arg Glu Asp Gly Ser Leu Asp
                485                 490                 495
Phe Gln Arg Gly Trp Lys Glu Tyr Lys Met Gly Phe Gly Asn Pro Ser
            500                 505                 510
Gly Glu Tyr Trp Leu Gly Asn Glu Phe Ile Phe Ala Ile Thr Ser Gln
            515                 520                 525
Arg Gln Tyr Met Leu Arg Ile Glu Leu Met Asp Trp Glu Gly Asn Arg
            530                 535                 540
Ala Tyr Ser Gln Tyr Asp Arg Phe His Ile Gly Asn Glu Lys Gln Asn
545                 550                 555                 560
Tyr Arg Leu Tyr Leu Lys Gly His Thr Gly Thr Ala Gly Lys Gln Ser
                565                 570                 575
Ser Leu Ile Leu His Gly Ala Asp Phe Ser Thr Lys Asp Ala Asp Asn
            580                 585                 590
Asp Asn Cys Met Cys Lys Cys Ala Leu Met Leu Thr Gly Gly Trp Trp
            595                 600                 605
```

Phe Asp Ala Cys Gly Pro Ser Asn Leu Asn Gly Met Phe Tyr Thr Ala
    610                 615                 620

Gly Gln Asn His Gly Lys Leu Asn Gly Ile Lys Trp His Tyr Phe Lys
625                 630                 635                 640

Gly Pro Ser Tyr Ser Leu Arg Ser Thr Thr Met Met Ile Arg Pro Leu
            645                 650                 655

Asp Phe

<210> SEQ ID NO 3
<211> LENGTH: 2025
<212> TYPE: DNA
<213> ORGANISM: Artificial Sequence
<220> FEATURE:
<223> OTHER INFORMATION: Synthetic

<400> SEQUENCE: 3

| | | | | | |
|---|---|---|---|---|---|
| agagactgtg | ctgaagtatt | caaatcagga | cacaccacaa | atggcatcta | cacgttaaca | 60 |
| ttccctaatt | ctacagaaga | gatcaaggcc | tactgtgaca | tggaagctgg | aggaggcggg | 120 |
| tggacaatta | ttcagcgacg | tgaggatggc | agcgttgatt | ttcagaggac | ttggaaagaa | 180 |
| tataaagtgg | gatttggtaa | cccttcagga | gaatattggc | tggaaatga | gtttgtttcg | 240 |
| caactgacta | atcagcaacg | ctatgtgctt | aaaatacacc | ttaaagactg | gaagggaat | 300 |
| gaggcttact | cattgtatga | acatttctat | ctctcaagtg | aagaactcaa | ttataggatt | 360 |
| caccttaaag | gacttacagg | gacagccggc | aaaataagca | gcatcagcca | accaggaaat | 420 |
| gattttagca | caaaggatgg | agacaacgac | aaatgtattt | gcaaatgttc | acaaatgcta | 480 |
| acaggaggct | ggtggtttga | tgcatgtggt | ccttccaact | gaacggaat | gtactatcca | 540 |
| cagaggcaga | acacaaataa | gttcaacggc | attaaatggt | actactgaa | aggctcaggc | 600 |
| tattcgctca | aggccacaac | catgatgatc | cgaccagcag | atttcggggg | cccgggcgag | 660 |
| cccaaatctt | gtgacaaaac | tcacacatgc | ccaccgtgcc | cagcacctga | actcctgggg | 720 |
| ggaccgtcag | tcttcctctt | ccccccaaaa | cccaaggaca | ccctcatgat | ctcccggacc | 780 |
| cctgaggtca | catgcgtggt | ggtggacgtg | agccacgaag | accctgaggt | caagttcaac | 840 |
| tggtacgtgg | acggcgtgga | ggtgcataat | gccaagacaa | agccgcggga | ggagcagtac | 900 |
| aacagcacgt | accgtgtggt | cagcgtcctc | accgtcctgc | accaggactg | gctgaatggc | 960 |
| aaggagtaca | agtgcaaggt | ctccaacaaa | gccctcccag | cccccatcga | gaaaaccatc | 1020 |
| tccaaagcca | aagggcagcc | ccgagaacca | caggtgtaca | ccctgccccc | atcccgggat | 1080 |
| gagctgacca | agaaccaggt | cagcctgacc | tgcctggtca | aaggcttcta | tcccagcgac | 1140 |
| atcgccgtgg | agtgggagag | caatgggcag | ccggagaaca | actacaagac | cacgcctccc | 1200 |
| gtgctggact | ccgacggctc | cttcttcctc | tacagcaagc | tcaccgtgga | caagagcagg | 1260 |
| tggcagcagg | ggaacgtctt | ctcatgctcc | gtgatgcatg | aggctctgca | caaccactac | 1320 |
| acgcagaaga | gcctctccct | gtctccgggt | aaaggcggtg | gcggttctgg | cgcgcctaga | 1380 |
| gactgtgctg | aagtattcaa | atcaggacac | accacaaatg | gcatctacac | gttaacattc | 1440 |
| cctaattcta | cagaagagat | caaggcctac | tgtgacatgg | aagctggagg | aggcgggtgg | 1500 |
| acaattattc | agcgacgtga | ggatggcagc | gttgattttc | agaggacttg | gaaagaatat | 1560 |
| aaagtgggat | ttggtaaccc | ttcaggagaa | tattggctgg | aaatgagtt | tgtttcgcaa | 1620 |
| ctgactaatc | agcaacgcta | tgtgcttaaa | atacacctta | aagactggga | agggaatgag | 1680 |
| gcttactcat | tgtatgaaca | tttctatctc | tcaagtgaag | aactcaatta | taggattcac | 1740 |

```
cttaaaggac ttacagggac agccggcaaa ataagcagca tcagccaacc aggaaatgat      1800
tttagcacaa aggatggaga caacgacaaa tgtatttgca atgttcaca aatgctaaca       1860 ggaggctggt ggtttgatgc atgtggtcct ccaacttga acggaatgta ctatccacag      1920
aggcagaaca caaataagtt caacggcatt aaatggtact actggaaagg ctcaggctat     1980
tcgctcaagg ccacaaccat gatgatccga ccagcagatt tctga                     2025
```

<210> SEQ ID NO 4
<211> LENGTH: 674
<212> TYPE: PRT
<213> ORGANISM: Artificial Sequence
<220> FEATURE:
<223> OTHER INFORMATION: Synthetic

<400> SEQUENCE: 4

```
Arg Asp Cys Ala Glu Val Phe Lys Ser Gly His Thr Thr Asn Gly Ile
1               5                   10                  15

Tyr Thr Leu Thr Phe Pro Asn Ser Thr Glu Glu Ile Lys Ala Tyr Cys
            20                  25                  30

Asp Met Glu Ala Gly Gly Gly Gly Trp Thr Ile Ile Gln Arg Arg Glu
        35                  40                  45

Asp Gly Ser Val Asp Phe Gln Arg Thr Trp Lys Glu Tyr Lys Val Gly
    50                  55                  60

Phe Gly Asn Pro Ser Gly Glu Tyr Trp Leu Gly Asn Glu Phe Val Ser
65                  70                  75                  80

Gln Leu Thr Asn Gln Gln Arg Tyr Val Leu Lys Ile His Leu Lys Asp
                85                  90                  95

Trp Glu Gly Asn Glu Ala Tyr Ser Leu Tyr Glu His Phe Tyr Leu Ser
            100                 105                 110

Ser Glu Glu Leu Asn Tyr Arg Ile His Leu Lys Gly Leu Thr Gly Thr
        115                 120                 125

Ala Gly Lys Ile Ser Ser Ile Ser Gln Pro Gly Asn Asp Phe Ser Thr
    130                 135                 140

Lys Asp Gly Asp Asn Asp Lys Cys Ile Cys Lys Cys Ser Gln Met Leu
145                 150                 155                 160

Thr Gly Gly Trp Trp Phe Asp Ala Cys Gly Pro Ser Asn Leu Asn Gly
                165                 170                 175

Met Tyr Tyr Pro Gln Arg Gln Asn Thr Asn Lys Phe Asn Gly Ile Lys
            180                 185                 190

Trp Tyr Tyr Trp Lys Gly Ser Gly Tyr Ser Leu Lys Ala Thr Thr Met
        195                 200                 205

Met Ile Arg Pro Ala Asp Phe Gly Gly Pro Gly Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
```

```
            305                 310                 315                 320
Lys Glu Tyr Lys Cys Lys Val Ser Asn Lys Ala Leu Pro Ala Pro Ile
                    325                 330                 335
Glu Lys Thr Ile Ser Lys Ala Lys Gly Gln Pro Arg Glu Pro Gln Val
                340                 345                 350
Tyr Thr Leu Pro Pro Ser Arg Asp Glu Leu Thr Lys Asn Gln Val Ser
            355                 360                 365
Leu Thr Cys Leu Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys Gly Gly Gly Ser Gly Ala Pro Arg Asp Cys Ala Glu
    450                 455                 460
Val Phe Lys Ser Gly His Thr Thr Asn Gly Ile Tyr Thr Leu Thr Phe
465                 470                 475                 480
Pro Asn Ser Thr Glu Glu Ile Lys Ala Tyr Cys Asp Met Glu Ala Gly
                485                 490                 495
Gly Gly Gly Trp Thr Ile Ile Gln Arg Arg Glu Asp Gly Ser Val Asp
            500                 505                 510
Phe Gln Arg Thr Trp Lys Glu Tyr Lys Val Gly Phe Gly Asn Pro Ser
        515                 520                 525
Gly Glu Tyr Trp Leu Gly Asn Glu Phe Val Ser Gln Leu Thr Asn Gln
    530                 535                 540
Gln Arg Tyr Val Leu Lys Ile His Leu Lys Asp Trp Glu Gly Asn Glu
545                 550                 555                 560
Ala Tyr Ser Leu Tyr Glu His Phe Tyr Leu Ser Ser Glu Glu Leu Asn
                565                 570                 575
Tyr Arg Ile His Leu Lys Gly Leu Thr Gly Thr Ala Gly Lys Ile Ser
            580                 585                 590
Ser Ile Ser Gln Pro Gly Asn Asp Phe Ser Thr Lys Asp Gly Asp Asn
        595                 600                 605
Asp Lys Cys Ile Cys Lys Cys Ser Gln Met Leu Thr Gly Gly Trp Trp
    610                 615                 620
Phe Asp Ala Cys Gly Pro Ser Asn Leu Asn Gly Met Tyr Tyr Pro Gln
625                 630                 635                 640
Arg Gln Asn Thr Asn Lys Phe Asn Gly Ile Lys Trp Tyr Tyr Trp Lys
                645                 650                 655
Gly Ser Gly Tyr Ser Leu Lys Ala Thr Thr Met Met Ile Arg Pro Ala
            660                 665                 670
Asp Phe

<210> SEQ ID NO 5
<211> LENGTH: 465
<212> TYPE: PRT
<213> ORGANISM: Artificial Sequence
<220> FEATURE:
<223> OTHER INFORMATION: Synthetic

<400> SEQUENCE: 5
```

```
Met Ser Ala Leu Leu Ile Leu Ala Leu Val Gly Ala Ala Val Ala Arg
1               5                   10                  15

Asp Cys Ala Asp Val Tyr Gln Ala Gly Phe Asn Lys Ser Gly Ile Tyr
            20                  25                  30

Thr Ile Tyr Ile Asn Asn Met Pro Glu Pro Lys Lys Val Phe Cys Asn
        35                  40                  45

Met Asp Val Asn Gly Gly Gly Trp Thr Val Ile Gln His Arg Glu Asp
    50                  55                  60

Gly Ser Leu Asp Phe Gln Arg Gly Trp Lys Glu Tyr Lys Met Gly Phe
65                  70                  75                  80

Gly Asn Pro Ser Gly Glu Tyr Trp Leu Gly Asn Glu Phe Ile Phe Ala
                85                  90                  95

Ile Thr Ser Gln Arg Gln Tyr Met Leu Arg Ile Glu Leu Met Asp Trp
        100                 105                 110

Glu Gly Asn Arg Ala Tyr Ser Gln Tyr Asp Arg Phe His Ile Gly Asn
            115                 120                 125

Glu Lys Gln Asn Tyr Arg Leu Tyr Leu Lys Gly His Thr Gly Thr Ala
    130                 135                 140

Gly Lys Gln Ser Ser Leu Ile Leu His Gly Ala Asp Phe Ser Thr Lys
145                 150                 155                 160

Asp Ala Asp Asn Asp Asn Cys Met Cys Lys Cys Ala Leu Met Leu Thr
                165                 170                 175

Gly Gly Trp Trp Phe Asp Ala Cys Gly Pro Ser Asn Leu Asn Gly Met
            180                 185                 190

Phe Tyr Thr Ala Gly Gln Asn His Gly Lys Leu Asn Gly Ile Lys Trp
        195                 200                 205

His Tyr Phe Lys Gly Pro Ser Tyr Ser Leu Arg Ser Thr Thr Met Met
    210                 215                 220

Ile Arg Pro Leu Asp Phe Gly Pro Gly Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
        260                 265                 270

Arg Thr Pro Glu Val Thr Cys Val Val Val Asp Val Ser His Glu Asp
    275                 280                 285

Pro Glu Val Lys Phe Asn Trp Tyr Val Asp Gly Val Glu Val His Asn
290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
        340                 345                 350

Thr Ile Ser Lys Ala Lys Gly Gln Pro Arg Glu Pro Gln Val Tyr Thr
    355                 360                 365

Leu Pro Pro Ser Arg Asp Glu Leu Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415
```

```
Asp Ser Asp Gly Ser Phe Phe Leu Tyr Ser Lys Leu Thr Val Asp Lys
                420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465

<210> SEQ ID NO 6
<211> LENGTH: 466
<212> TYPE: PRT
<213> ORGANISM: Artificial Sequence
<220> FEATURE:
<223> OTHER INFORMATION: Synthetic

<400> SEQUENCE: 6

Met Ser Ala Leu Leu Ile Leu Ala Leu Val Gly Ala Ala Val Ala Arg
1               5                   10                  15

Asp Cys Ala Glu Val Phe Lys Ser Gly His Thr Thr Asn Gly Ile Tyr
            20                  25                  30

Thr Leu Thr Phe Pro Asn Ser Thr Glu Glu Ile Lys Ala Tyr Cys Asp
        35                  40                  45

Met Glu Ala Gly Gly Gly Gly Trp Thr Ile Ile Gln Arg Arg Glu Asp
    50                  55                  60

Gly Ser Val Asp Phe Gln Arg Thr Trp Lys Glu Tyr Lys Val Gly Phe
65                  70                  75                  80

Gly Asn Pro Ser Gly Glu Tyr Trp Leu Gly Asn Glu Phe Val Ser Gln
                85                  90                  95

Leu Thr Asn Gln Gln Arg Tyr Val Leu Lys Ile His Leu Lys Asp Trp
            100                 105                 110

Glu Gly Asn Glu Ala Tyr Ser Leu Tyr Glu His Phe Tyr Leu Ser Ser
        115                 120                 125

Glu Glu Leu Asn Tyr Arg Ile His Leu Lys Gly Leu Thr Gly Thr Ala
    130                 135                 140

Gly Lys Ile Ser Ser Ile Ser Gln Pro Gly Asn Asp Phe Ser Thr Lys
145                 150                 155                 160

Asp Gly Asp Asn Asp Lys Cys Ile Cys Lys Cys Ser Gln Met Leu Thr
                165                 170                 175

Gly Gly Trp Trp Phe Asp Ala Cys Gly Pro Ser Asn Leu Asn Gly Met
            180                 185                 190

Tyr Tyr Pro Gln Arg Gln Asn Thr Asn Lys Phe Asn Gly Ile Lys Trp
        195                 200                 205

Tyr Tyr Trp Lys Gly Ser Gly Tyr Ser Leu Lys Ala Thr Thr Met Met
    210                 215                 220

Ile Arg Pro Ala Asp Phe Gly Pro Gly Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300
```

```
Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
            325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
            405                 410                 415

Leu Asp Ser Asp Gly Ser Phe Phe Leu Tyr Ser Lys Leu Thr Val Asp
        420                 425                 430

Lys Ser Arg Trp Gln Gln Gly Asn Val Phe Ser Cys Ser Val Met His
    435                 440                 445

Glu Ala Leu His Asn His Tyr Thr Gln Lys Ser Leu Ser Leu Ser Pro
450                 455                 460

Gly Lys
465

<210> SEQ ID NO 7
<211> LENGTH: 466
<212> TYPE: PRT
<213> ORGANISM: Artificial Sequence
<220> FEATURE:
<223> OTHER INFORMATION: Synthetic

<400> SEQUENCE: 7

Met Ser Ala Leu Leu Ile Leu Ala Leu Val Gly Ala Ala Val Ala Arg
1               5                   10                  15

Asp Cys Ala Glu Val Phe Lys Ser Gly His Thr Thr Asn Gly Ile Tyr
            20                  25                  30

Thr Leu Thr Phe Pro Asn Ser Thr Glu Glu Ile Lys Ala Tyr Cys Asp
        35                  40                  45

Met Glu Ala Gly Gly Gly Gly Trp Thr Ile Ile Gln Arg Arg Glu Asp
50                  55                  60

Gly Ser Val Asp Phe Gln Arg Thr Trp Lys Glu Tyr Lys Val Gly Phe
65                  70                  75                  80

Gly Asn Pro Ser Gly Glu Tyr Trp Leu Gly Asn Glu Phe Val Ser Gln
            85                  90                  95

Leu Thr Asn Gln Gln Arg Tyr Val Leu Lys Ile His Leu Lys Asp Trp
        100                 105                 110

Glu Gly Asn Glu Ala Tyr Ser Leu Tyr Glu His Phe Tyr Leu Ser Ser
    115                 120                 125

Glu Glu Leu Asn Tyr Arg Ile His Leu Lys Gly Leu Thr Gly Thr Ala
130                 135                 140

Gly Lys Ile Ser Ser Ile Ser Gln Pro Gly Asn Asp Phe Ser Thr Lys
145                 150                 155                 160

Asp Gly Asp Asn Asp Lys Cys Ile Cys Lys Cys Ser Gln Met Leu Thr
            165                 170                 175

Gly Gly Trp Trp Phe Asp Ala Cys Gly Pro Ser Asn Leu Asn Gly Met
        180                 185                 190
```

Tyr Tyr Pro Gln Arg Gln Asn Thr Asn Lys Ala Asn Gly Ile Lys Trp
            195                 200                 205

Ala Ala Trp Lys Gly Ser Gly Tyr Ser Leu Lys Ala Thr Thr Met Met
    210                 215                 220

Ile Arg Pro Ala Asp Phe Gly Pro Gly Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
                275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
                340                 345                 350

Lys Thr Ile Ser Lys Ala Lys Gly Gln Pro Arg Glu Pro Gln Val Tyr
                355                 360                 365

Thr Leu Pro Pro Ser Arg Asp Glu Leu Thr Lys Asn Gln Val Ser Leu
                370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
                420                 425                 430

Lys Ser Arg Trp Gln Gln Gly Asn Val Phe Ser Cys Ser Val Met His
                435                 440                 445

Glu Ala Leu His Asn His Tyr Thr Gln Lys Ser Leu Ser Leu Ser Pro
    450                 455                 460

Gly Lys
465

<210> SEQ ID NO 8
<211> LENGTH: 19
<212> TYPE: DNA
<213> ORGANISM: Artificial Sequence
<220> FEATURE:
<223> OTHER INFORMATION: Synthetic

<400> SEQUENCE: 8
tgaagtacct gatattcta                                              19

<210> SEQ ID NO 9
<211> LENGTH: 748
<212> TYPE: PRT
<213> ORGANISM: Artificial Sequence
<220> FEATURE:
<223> OTHER INFORMATION: Synthetic

<400> SEQUENCE: 9

Met Asp Ser Leu Ala Ser Leu Val Leu Cys Gly Val Ser Leu Leu Leu
1               5                   10                  15

-continued

```
Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
                35                  40                  45

Trp Arg Pro His Glu Pro Ile Thr Ile Gly Arg Asp Phe Glu Ala Leu
         50                  55                  60

Met Asn Gln His Gln Asp Pro Leu Glu Val Thr Gln Asp Val Thr Arg
 65                  70                  75                  80

Glu Trp Ala Lys Lys Val Val Trp Lys Arg Glu Lys Ala Ser Lys Ile
                 85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Pro Arg Met Thr Pro Lys Ile
            340                 345                 350

Val Asp Leu Pro Asp His Ile Glu Val Asn Ser Gly Lys Phe Asn Pro
        355                 360                 365

Ile Cys Lys Ala Ser Gly Trp Pro Leu Pro Thr Asn Glu Glu Met Thr
370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                405                 410                 415

Pro Asp Ser Gly Val Trp Val Cys Ser Val Asn Thr Val Ala Gly Met
            420                 425                 430

Val Glu Lys Pro Phe Asn Ile Ser Val Lys Val Leu Pro Lys Pro Leu
```

-continued

```
                    435                 440                 445
Asn Ala Pro Asn Val Ile Asp Thr Gly His Asn Phe Ala Val Ile Asn
        450                 455                 460
Ile Ser Ser Glu Pro Tyr Phe Gly Asp Gly Pro Ile Lys Ser Lys Lys
465                 470                 475                 480
Leu Leu Tyr Lys Pro Val Asn His Tyr Glu Ala Trp Gln His Ile Gln
                485                 490                 495
Val Thr Asn Glu Ile Val Thr Leu Asn Tyr Leu Glu Pro Arg Thr Glu
            500                 505                 510
Tyr Glu Leu Cys Val Gln Leu Val Arg Arg Gly Glu Gly Gly Glu Gly
            515                 520                 525
His Pro Gly Pro Val Arg Arg Phe Thr Thr Ala Ser Ile Gly Leu Pro
            530                 535                 540
Pro Pro Arg Gly Leu Asn Leu Leu Pro Lys Ser Gln Thr Thr Leu Asn
545                 550                 555                 560
Leu Thr Trp Gln Pro Ile Phe Pro Ser Ser Glu Asp Asp Phe Tyr Val
                565                 570                 575
Glu Val Glu Arg Arg Ser Val Gln Lys Ser Asp Gln Gln Asn Ile Lys
            580                 585                 590
Val Pro Gly Asn Leu Thr Ser Val Leu Leu Asn Asn Leu His Pro Arg
            595                 600                 605
Glu Gln Tyr Val Val Arg Ala Arg Val Asn Thr Lys Ala Gln Gly Glu
        610                 615                 620
Trp Ser Glu Asp Leu Thr Ala Trp Thr Leu Ser Asp Ile Leu Pro Pro
625                 630                 635                 640
Gln Pro Glu Asn Ile Lys Ile Ser Asn Ile Thr His Ser Ser Ala Val
                645                 650                 655
Ile Ser Trp Thr Ile Leu Asp Gly Tyr Ser Ile Ser Ser Ile Thr Ile
                660                 665                 670
Arg Tyr Lys Val Gln Gly Lys Asn Glu Asp Gln His Val Asp Val Lys
            675                 680                 685
Ile Lys Asn Ala Thr Ile Thr Gln Tyr Gln Leu Lys Gly Leu Glu Pro
        690                 695                 700
Glu Thr Ala Tyr Gln Val Asp Ile Phe Ala Glu Asn Asn Ile Gly Ser
705                 710                 715                 720
Ser Asn Pro Ala Phe Ser His Glu Leu Val Thr Leu Pro Glu Ser Gln
                725                 730                 735
Ala Pro Ala Asp Leu Gly Gly Gly Lys Met Leu Leu
            740                 745
```

USE OF ANGIOPOIETINS IN PROMOTING BLOOD COAGULATION AND IN THE TREATMENT OF BLOOD COAGULATION DISORDERS

CROSS-REFERENCE TO RELATED APPLICATIONS

This Application is a US National Stage Application under 35 USC § 371 of PCT/US2016/060527, filed Nov. 4, 2016, which claims the benefit under 35 USC § 119(e) of U.S. Provisional Patent Application No. 62/252,217, filed Nov. 6, 2015, each of which is herein incorporated by reference in its entirety.

REFERENCE TO A SEQUENCE LISTING

This application incorporates by reference the Sequence Listing submitted in Computer Readable Form as file 10194WO01-Sequence.txt, created on Oct. 31, 2016, and containing 36,151 bytes.

FIELD OF THE INVENTION

The present invention resides in the field of medicine, and relates to the use of angiopoietin molecules or variants thereof to promote blood coagulation and/or treat blood coagulation disorders in a subject in need thereof.

BACKGROUND

Excessive bleeding or slowed blood coagulation leads to death or debilitation for patients. Blood coagulation disorders in humans are caused by inborn genetic conditions or may be a side effect of drug treatment for other conditions. Blood loss may occur during surgery or after injury. Injury is the second leading cause of death for people aged five to 45 years, and over four million people worldwide die of injuries every year, often because of extensive blood loss. Current treatment options include adsorbent chemicals (such as zeolites, e.g., QuikClot), other hemostatic agents (such as microfibrillar collagen hemostat (MCH), chitosan hemostat, and styptics), thrombin, fibrin glue, desmopressin, coagulation factor concentrates, prothrombin complex concentrate, cryoprecipitate, fresh frozen plasma, recombinant Factor VII, and antifibrinolytic drugs such as tranexamic acid (TXA), epsilon-aminocaproic acid and aminomethylbenzoic acid. Mechanical devices, such as a hemostatic clamp, are also used. There remains a need for effective therapeutic and preventive approaches to promote blood coagulation or treat blood coagulation disorders.

BRIEF SUMMARY OF THE INVENTION

According to one aspect of the present invention, methods are provided for stimulating blood coagulation, or treating, preventing or ameliorating at least one symptom, indication or complication of a blood coagulation disorder in a subject in need thereof. The present invention is predicated, in part, on the discovery that both angiopoietin-1 (Ang1) and angiopoietin-2 (Ang2) bind to and modulate the function of thrombomodulin (TM), an endothelial cell surface molecule that plays an essential role as a coagulation regulator. TM functions as a cofactor in the thrombin-mediated activation of protein C, an anticoagulant protein, and of thrombin-activatable fibrinolysis inhibitor (TAFI), an inhibitor of blood clot dissolution. As detailed in the Examples and the discussion below, both Ang1 and Ang2 inhibited activation of protein C and TAFI in cultured endothelial cells, and inhibited the binding of thrombin to TM in vitro. These results suggest a previously undescribed role for angiopoietins in the regulation of hemostasis.

In one aspect, the present invention provides a method of treating, preventing or ameliorating at least one symptom, indication or complication of a blood coagulation disorder comprising administering to a subject in need thereof a pharmaceutical composition comprising a therapeutically effective amount of an angiopoietin protein and a pharmaceutically acceptable carrier. In another aspect, the present invention provides for the use of a therapeutically effective amount of an angiopoietin protein (i) for treating, preventing or ameliorating at least one symptom, indication or complication of a blood coagulation disorder, or (ii) in the manufacture of a medicament for treating, preventing or ameliorating at least one symptom, indication or complication of a blood coagulation disorder.

In one embodiment, the blood coagulation disorder is selected from the group consisting of inborn platelet pathologies such as thrombasthenia of Glanzmann and Naegeli (Glanzmann thrombasthenia), Bernard-Soulier syndrome (abnormal glycoprotein Ib-IX-V complex), gray platelet syndrome (deficient alpha granules), delta storage pool deficiency (deficient dense granules), and Von Willebrand disease; platelet disorders caused by insufficient production including myelodysplastic syndrome or other bone marrow disorders or by destruction by the immune system including immune thrombocytopenic purpura/ITP; coagulation factor disorders such as hemophilias including hemophilia A (factor VIII deficiency), hemophilia B (factor IX deficiency or "Christmas disease") and hemophilia C (factor XI deficiency, mild bleeding tendency); deficiency of Vitamin K, Factor XII mutations, thrombocytopenia, uremia, and congenital afibrinogenemia; liver failure including acute, chronic, early and end-stage; and disorders associated with warfarin treatment, aspirin treatment, surgery, and injury.

In another aspect, the present invention provides a method of stimulating blood coagulation, comprising administering to a subject in need thereof a pharmaceutical composition comprising a therapeutically effective amount of an angiopoietin protein and a pharmaceutically acceptable carrier. In one embodiment, the subject is undergoing surgery. In one embodiment, the subject is bleeding due to injury. In yet another aspect, the present invention provides for the use of a therapeutically effective amount of an angiopoietin protein (i) for stimulating blood coagulation, or (ii) in the manufacture of a medicament for stimulating blood coagulation.

In some cases, the angiopoietin protein is administered at a site of injury or a site associated with a surgical procedure.

In various embodiments of the methods and uses discussed above, the angiopoietin protein of the pharmaceutical composition may be specified binding properties and/or comprise a native or modified angiopoietin protein.

In an embodiment, the angiopoietin protein binds a purified soluble extracellular domain of thrombomodulin with an $EC_{50}$ value of less than 100 nM.

In some cases, the angiopoietin protein is hAng1. In other cases, the angiopoietin protein is hAng2. In an embodiment, the angiopoietin protein is a modified angiopoietin protein.

In some embodiments, the modified angiopoietin protein comprises a fusion protein comprising angiopoietin-1 or a fragment thereof fused to a multimerizing domain. In some cases, the multimerizing domain is an immunoglobulin Fc fragment. In an embodiment, the fusion protein comprises at least one fibrinogen-like domain of angiopoietin-1 fused to an Fc fragment. For example, the fusion protein may comprise a first fibrinogen-like domain of angiopoietin-1 fused at its C-terminal end to the N-terminal end of an Fc fragment and the Fc fragment fused at its C-terminal end to the N-terminal end of a second fibrinogen-like domain of angiopoietin-1. In some cases, the modified angiopoietin is AngF1-Fc-F1. In one embodiment, the modified angiopoietin comprises an amino acid sequence of SEQ ID NO: 2.

In some embodiments, the modified angiopoietin protein comprises a fusion protein comprising angiopoietin-2 or a fragment thereof fused to a multimerizing domain. In some cases, the multimerizing domain is an immunoglobulin Fc fragment. In an embodiment, the fusion protein comprises at least one fibrinogen-like domain of angiopoietin-2 fused to an Fc fragment. For example, the fusion protein may comprise a first fibrinogen-like domain of angiopoietin-2 fused at its C-terminal end to the N-terminal end of an Fc fragment and the Fc fragment fused at its C-terminal end to the N-terminal end of a second fibrinogen-like domain of angiopoietin-2. In some cases, the modified angiopoietin is AngF2-Fc-F2. In one embodiment, the modified angiopoietin comprises an amino acid sequence of SEQ ID NO:4.

In some cases, the angiopoietin protein is administered intravenously. In some cases, the angiopoietin protein is administered subcutaneously.

In certain embodiments, the angiopoietin is administered in combination with a second therapeutic agent or therapy.

Other embodiments of the present invention will become apparent from a review of the ensuing detailed description.

BRIEF DESCRIPTION OF THE FIGURES

FIG. 1A shows that Ang1-FD-Fc and Ang2-FD-Fc bind saturably to COS cells overexpressing TM; FIG. 1B shows that BowAng1 and BowAng2 bind the soluble extracellular domains of either TM or Tie2; FIG. 1C shows that soluble Tie2 extracellular domain competes with the soluble extracellular domain of TM for binding to BowAng1 or BowAng2.

FIG. 2A shows that native Ang1 and Ang2 inhibit TM-dependent formation of APC in cultured HUVECs; FIG. 2B shows that native Ang1 inhibits TM-dependent formation of APC, while PF4 increases TM-dependent formation of APC, in cultured HUVECs; FIG. 2C shows that native Ang1 and Ang2 inhibit TM-dependent formation of aTAFI in cultured HUVECs; FIG. 2D shows that native Ang1 and Ang2 inhibit TM-dependent formation of APC in COS cells overexpressing TM but lacking Tie2 expression; FIG. 2E shows that native Ang1 and Ang2 inhibit TM-dependent formation of aTAFI in COS cells overexpressing TM but lacking Tie2 expression.

FIG. 3A shows inhibition of Tie2 expression in HUVECs infected with adenovirus encoding a Tie2 specific shRNA; FIG. 3B shows that native Ang1 inhibits TM-dependent formation of APC in HUVECs infected with adenovirus encoding a Tie2 specific shRNA.

FIG. 4A shows that native Ang1 inhibits association of thrombin to soluble extracellular domain of TM; FIG. 4B shows that native Ang2 inhibits association of thrombin to soluble extracellular domain of TM.

FIGS. 5A, 5B, 5C and 5D show that Ang1 is present in platelets and is released upon activation: FIG. 5A shows that Ang1 is present in mouse platelets; FIG. 5B shows that Ang1 levels are higher in mouse serum than in mouse plasma; FIG. 5C shows that Ang1 levels are higher in plasma prepared from mice treated with thrombin compared to plasma prepared from untreated mice; FIG. 5D shows that Ang1 levels are higher in plasma prepared from blood collected at the site of tail nicks in mice compared to plasma prepared blood collected by cardiac puncture in mice (systemic).

FIGS. 6A and 6B show that intravenous administration of BowAng1 and BowAng2 to mice promotes a rapid increase in circulating thrombin/antithrombin level and fibrin deposition in lung: FIG. 6A shows that BowAng1 and BowAng2 promote an increase in fibrin deposition in lung tissue in mice; FIG. 6B shows that BowAng1 and BowAng2 promote an increase in circulating thrombin/antithrombin level in mice.

DETAILED DESCRIPTION

Figure 1B:
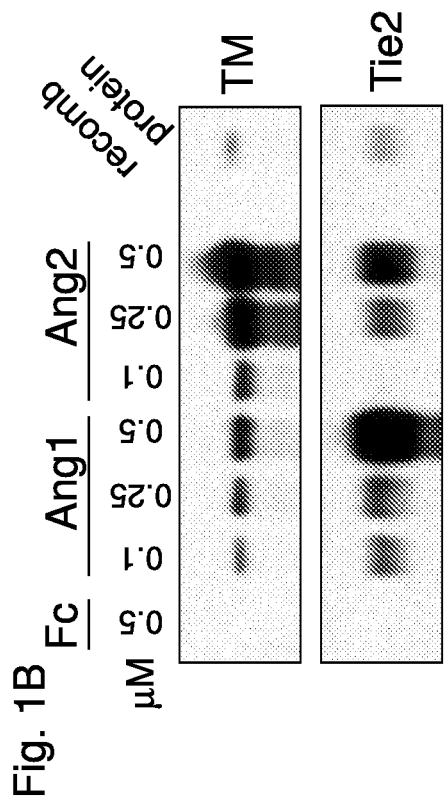
FIGS. 1A, 1B and 1C show that Ang1 and Ang2 interact with TM via their fibrinogen-like domains.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present invention, the preferred methods and materials are now described. All publications mentioned herein are incorporated herein by reference in their entirety.

Definitions

As used herein, an "angiopoietin" includes Angiopoietin-1 (Ang1) or Angiopoietin-2 (Ang2), unless otherwise specified. The term "hAng1" refers to human Ang1, and the term "hAng2" refers to human Ang2.

The term "$EC_{50}$" or "EC50", as used herein, refers to the half maximal effective concentration, which includes the concentration of a ligand that induces a response, for example a cellular response, halfway between the baseline and maximum after a specified exposure time. The $EC_{50}$ essentially represents the concentration of a ligand where 50% of its maximal effect is observed.

The term "$IC_{50}$" or "IC50", as used herein, refers to the half maximal inhibitory concentration of a cellular response. In other words, the measure of the effectiveness of a particular moiety (e.g. protein, compound, or molecule) in inhibiting biological or biochemical function, wherein an assay quantitates the amount of such moiety needed to inhibit a given biological process.

The terms "modified angiopoietin" or "modified angiopoietin protein" refer to recombinant angiopoietins (e.g., angiopoietin expressed in an adenoviral vector; Thurston et al 2000, Nat. Med.), mutant and chimeric forms of angiopoietins, and fusion proteins comprising angiopoietin or a fragment thereof that specifically bind thrombomodulin TM.

The terms "native Ang1" and "native Ang2," as used herein, refer to a full-length Ang1 or Ang2, respectively, without N-terminal signal peptide.

The term "preventing," as used herein refers to preventing development of a symptom, indication or complication of a blood coagulation disorder.

As used herein, the term "subject" refers to an animal, preferably a mammal, that exhibits one or more symptoms, indications or complications of a blood coagulation disorder, and/or who has been diagnosed with a blood coagulation disorder and/or is in need of amelioration, prevention and/or treatment of a blood coagulation disorder. The term "a subject in need thereof" may also include, e.g., subjects who, prior to treatment, exhibit (or have exhibited) one or more symptoms or indications of a blood coagulation disorder including but not limited to excessive bleeding and slow blood coagulation time.

As used herein, the terms "treat", "treating", or the like, mean to alleviate a symptom or a complication, eliminate the causation of a symptom or a complication either on a temporary or permanent basis, or to prevent or slow the appearance of a symptom or complication of a blood coagulation disorder in the subject. In the context of the present invention, the terms "treat", "treating", or the like, refer to e.g., reducing bleeding or reducing time needed to coagulate blood in a patient in need thereof.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

Methods for Treating, Preventing or Ameliorating Blood Coagulation Disorders or Promoting Blood Coagulation.

The angiopoietins were identified as ligands for the endothelial-specific receptor tyrosine kinase, Tie2. Angiopoietin/Tie2 signaling profoundly influences angiogenic processes, both during development and in the adult, for example in tumor vasculature. Angiopoietins have not previously been implicated in any processes other than the regulation of blood vessel formation and function via modulation of Tie2 activity.

As shown herein, both Angiopoietin-1 (Ang1) and Angiopoietin-2 (Ang2) bind to and modulate the function of thrombomodulin TM, an endothelial cell surface molecule that plays an essential role as a coagulation regulator. TM functions as a cofactor in the thrombin-mediated activation of protein C, an anticoagulant protein (Esmon, C. T., et al., 1982, J. Biol. Chem. 257:7944-7947; Owen, W. G., et al., 1981, J. Biol. Chem. 256:5532-5535; Van de Wouwer, M., et al., 2004, Arteriosclerosis, thrombosis, and vascular biology, 24:1374-1383; Weiler-Guettler, H., et al., 1998, The Journal of clinical investigation, 101:1983-1991; Esmon, C. T., 1981, Proc. Natl. Acad. Sci. U.S.A., 78:2249-2252), and of thrombin-activatable fibrinolysis inhibitor (TAFI), an inhibitor of blood clot dissolution.

As demonstrated in the examples, Ang1 and Ang2 inhibited both activation of protein C and TAFI in cultured endothelial cells, and inhibited the binding of thrombin to TM in vitro. Administration of thrombin to mice rapidly increased plasma Ang1 levels, and Ang1 levels were significantly elevated in plasma prepared from wound blood. Further, administration of a modified angiopoietin promoted a rapid increase in circulating thrombin/antithrombin level and fibrin deposition in the lungs of mice. These results indicate a previously undescribed role for angiopoietins in the regulation of hemostasis.

Accordingly, the present invention provides methods for treating, preventing or ameliorating at least one symptom, indication or complication of a blood coagulation disorder, or stimulating blood coagulation, in a subject. The methods according to these aspects of the invention comprise administering a therapeutically effective amount of a pharmaceutical composition comprising an angiopoietin protein or a modified angiopoietin protein to a subject in need thereof.

In various embodiments, the blood coagulation disorder may include, but is not limited to, inborn platelet pathologies such as thrombasthenia of Glanzmann and Naegeli (Glanzmann thrombasthenia), Bernard-Soulier syndrome (abnormal glycoprotein Ib-IX-V complex), gray platelet syndrome (deficient alpha granules), delta storage pool deficiency (deficient dense granules), and Von Willebrand disease. Blood coagulation disorders also include but are not limited to, platelet disorders caused by insufficient production (e.g., in myelodysplastic syndrome or other bone marrow disorders) or destruction by the immune system (immune thrombocytopenic purpura/ITP). Blood coagulation disorders also include, but are not limited to, coagulation factor disorders such as hemophilias including hemophilia A (factor VIII deficiency), hemophilia B (factor IX deficiency or "Christmas disease") and hemophilia C (factor XI deficiency, mild bleeding tendency). Blood coagulation disorders also include, but are not limited to, deficiency of Vitamin K, Factor XII mutations, thrombocytopenia, uremia, and congenital afibrinogenemia. Deficiencies in blood coagulation may also be associated with liver failure (acute and chronic forms, early liver failure, end-stage liver failure).

Bleeding or excessive bleeding may also be associated with treatment of a patient with warfarin or aspirin, or may occur during surgery or after injury. In particular embodiments, promotion of blood coagulation at a site of injury or surgery is contemplated.

The present invention includes methods for treating, preventing or reducing the severity of a blood coagulation disorder, or stimulating blood coagulation, comprising administering a therapeutically effective amount of a pharmaceutical composition comprising an angiopoietin protein or a modified angiopoietin protein to a subject in need thereof, wherein the pharmaceutical composition is administered to the subject in a single dose, or in multiple doses, e.g., as part of a specific therapeutic dosing regimen. For example, the therapeutic dosing regimen may comprise administering multiple doses of the pharmaceutical composition to the subject at a frequency of about once a day, once every two days, once every three days, once every four days, once every five days, once every six days, once a week, once every two weeks, once every three weeks, once every four weeks, once a month, once every two months, once every three months, once every four months, or less frequently. In some embodiments, the therapeutic dosing regimen comprises administering multiple doses of the pharmaceutical composition to the subject at a frequency of about once a day, about 2 times a day, about 3 times a day or more than 4 times a day.

In certain embodiments the angiopoietin protein or modified angiopoietin protein is administered subcutaneously, intravenously, intracranially, intraventricularly, or delivered systemically in an adenoviral vector to a subject in need thereof. In certain embodiments the angiopoietin protein or modified angiopoietin protein is administered at a site of injury or a site associated with a surgical procedure. In one embodiment, administration at a site of injury or surgery is by injection. In some cases, the site-specific administration of the angiopoietin protein or modified angiopoietin protein results in a high relative concentration of angiopoietin at the site to promote blood coagulation. In one embodiment, the "high relative concentration" is measured against plasma levels of angiopoietin, and may be, for example, greater than 10 nM, greater than 50 nM or greater than 100 nM.

Modified Angiopoietins

The methods of the present invention comprise administering to a subject in need thereof a therapeutic composition comprising an angiopoietin or a variant thereof. In some cases, the variant angiopoietin is a modified angiopoietin.

Non-limiting examples of categories of modified angiopoietins include recombinant angiopoietins (e.g., angiopoietin expressed in an adenoviral vector; Thurston et al 2000, Nat. Med.), mutant and chimeric forms of angiopoietins, and fusion proteins comprising angiopoietin or a fragment thereof that specifically bind thrombomodulin TM.

According to certain exemplary embodiments of the present invention, the modified angiopoietin is a fusion protein comprising one or more domains of the angiopoietin molecule fused to a multimerizing domain. In general terms, the multimerizing domain(s) of the present invention function to connect the various components of the angiopoietin molecule (e.g., the fibrinogen-like domains) with one another. As used herein, a "multimerizing domain" is any macromolecule that has the ability to associate (covalently or non-covalently) with a second macromolecule of the same or similar structure or constitution. For example, a multimerizing domain may be a polypeptide comprising an immunoglobulin $C_H3$ domain. A non-limiting example of a multimerizing domain is an Fc portion of an immunoglobulin, e.g., an Fc domain of an IgG selected from the isotypes IgG1, IgG2, IgG3, and IgG4, as well as any allotype within each isotype group. In certain embodiments, the multimerizing domain is an Fc fragment or an amino acid sequence of 1 to about 200 amino acids in length containing at least one cysteine residues. In other embodiments, the multimerizing domain is a cysteine residue or a short cysteine-containing peptide. Other multimerizing domains include peptides or polypeptides comprising or consisting of a leucine zipper, a helix-loop motif, or a coiled-coil motif.

In certain embodiments, the modified angiopoietin is a fusion protein comprising one or more fibrinogen-like domains of the angiopoietin-1 molecule fused to the Fc fragment of an immunoglobulin comprising any of the amino acid sequences, as set forth in U.S. Pat. No. 7,008,781. In certain exemplary embodiments, the fusion protein that can be used in the context of the methods of the present invention comprises a first fibrinogen-like domain of angiopoietin fused at its C-terminal end to the N-terminal end of an IgG Fc fragment and the C-terminal of the Fc fragment fused to the N-terminal end of a second fibrinogen-like domain of angiopoietin (Davis, S., et al, 2003; Nat. Struct. Biol. 10:38-44), wherein the angiopoietin may be Ang1 or Ang2. According to certain exemplary embodiments, the methods of the present invention comprise the use of the modified angiopoietin referred to and known in the art as AngF1-Fc-F1. In certain embodiments, the modified angiopoietin is a dimer comprising two AngF1-Fc-F1s that associate through intramolecular association of the Fc fragments (also referred to as BowAng1, as disclosed in Davis, 2003, supra. According to certain embodiments, the fusion protein comprises the amino acid sequence of SEQ ID NO: 2. According to certain exemplary embodiments, the methods of the present invention comprise the use of the modified angiopoietin referred to and known in the art as AngF2-Fc-F2. In certain embodiments, the modified angiopoietin is a dimer comprising two AngF2-Fc-F2s that associate through intramolecular association of the Fc fragments (also referred to as BowAng2, as disclosed in Davis, 2003, supra). In some embodiments, the fusion protein comprises the amino acid sequence of SEQ ID NO: 4. BowAng1 and BowAng2 contain the Ang1 or Ang2 fibrinogen domain followed by human Fc and another fibrinogen domain, so that following Fc-mediated dimerization, the proteins contain 4 angiopoietin fibrinogen domains (Davis, 2003, supra).

Other modified angiopoietins that can be used in the context of the methods of the present invention include any of the modified angiopoietin molecules as set forth in U.S. Pat. Nos. 6,265,564, 6,441,137, and 6,825,008.

The present invention includes modified angiopoietins that bind purified soluble extracellular domain of TM with an $EC_{50}$ value of less than about 100 nM, as measured by an in vitro assay, e.g., using the assay format as defined in Example 3 herein (e.g., assessing the ability of modified angiopoietins to bind purified soluble extracellular domain of TM), or a substantially similar assay. In certain embodiments, the modified angiopoietins of the present invention bind purified soluble extracellular domain of TM), with an $EC_{50}$ value of less than about 90 nM, 80 nM, 70 nM, 60 nM, 50 nM, 40 nM, 30 nM, 20 nM or 10 nM as measured by an in vitro assay, e.g., using the assay format as defined in Example 3 herein (e.g., assessing the ability of modified angiopoietins to bind purified soluble extracellular domain of TM), or a substantially similar assay.

The present invention includes modified angiopoietins that inhibit APC formation in cultured HUVECs with an $IC_{50}$ of less than about 100 nM as measured by an cell-based assay, e.g., using the assay format as defined in Example 5 herein (e.g., assessing the ability of modified angiopoietins to inhibit APC formation in cultured HUVECs), or a substantially similar assay. In certain embodiments, the modified angiopoietins of the present invention inhibit APC formation in a cultured HUVECs with an $10_{50}$ of less than about 90 nM, 80 nM, 70 nM, 60 nM, 50 nM, 40 nM, 30 nM, 20 nM or 10 nM as measured by an cell-based assay, e.g., using the assay format as defined in Example 5 herein (e.g., assessing the ability of modified angiopoietins to inhibit APC formation in cultured HUVECs), or a substantially similar assay.

Pharmaceutical Compositions

The present invention includes methods which comprise administering an angiopoietin protein or a modified angiopoietin protein to a subject wherein the angiopoietin protein or modified angiopoietin protein is contained within a pharmaceutical composition. The pharmaceutical compositions of the invention may be formulated with suitable carriers (e.g., pharmaceutically acceptably carriers), excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262: 4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used. In another embodiment, polymeric materials can be used; see, Medical Applications of Controlled Release, Langer and Wise (eds.), 1984, CRC Press, Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the angiopoietin protein or modified angiopoietin protein described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Dosage

The amount of the angiopoietin protein or modified angiopoietin protein (e.g., AngF1-Fc-F1 or AngF2-Fc-F2) administered to a subject according to the methods of the present invention is, generally, a therapeutically effective amount. As used herein, the phrase "therapeutically effective amount" means an amount of the angiopoietin protein or modified angiopoietin protein that results in reduction in the severity or duration of a symptom, indication or complication of a blood coagulation disorder, or promotes blood coagulation.

In the case of an angiopoietin protein or a modified angiopoietin protein, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the angiopoietin protein or modified angiopoietin protein.

The amount of the angiopoietin protein or modified angiopoietin protein contained within the individual doses may be expressed in terms of milligrams of protein per kilogram of the subject's body weight (i.e., mg/kg). For example, the modified angiopoietin may be administered to a subject at a dose of about 0.0001 to about 100 mg/kg of patient body weight. In certain embodiments, the angiopoietin protein or modified angiopoietin protein is administered to a subject in need thereof at a dose of about 5-25 mg/kg of the subject's body weight.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for.

Unless indicated otherwise, parts are parts by weight, molecular weight is average molecular weight, temperature is in degrees Centigrade, and pressure is at or near atmospheric.

Example 1. Thrombomodulin Binds Ang1-FD-Fc in Expression Cloning Study cDNA expression libraries were constructed in the expression vector pJFE with mRNA isolated from human umbilical vein endothelial cells (HUVECs) and from the endothelial-like cell line EA.hy926, using a kit (Invitrogen). The libraries were transfected into dishes of COS cells and screened as in Davis, S., et al., (1994; Science. 266:816-819) with the chimeric molecule Ang1-FD-Fc, consisting of the Tie2-binding fibrinogen-like domain (FD) of Ang1 fused to a human Fc tag (Davis, 2003, supra, SEQ ID NO:5), at a concentration of 1 µg/ml. Stained cells were rescued, and plasmid DNA extracted from them was progressively enriched until isolated clones were obtained. Out of eight independent clones, one of the associated cDNAs coded for Tie2, and the other seven clones, differing only in the length of untranslated regions, contained cDNAs encoding thrombomodulin TM, a cell surface protein highly expressed in endothelial cells (Esmon, 1981, supra). Only rare cells were stained on dishes of library-transfected COS cells, indicating that Ang1-FD-Fc binding to Tie2 and TM is highly specific.

Example 2. Ang1-FD-Fc and Ang2-FD-Fc Bind Saturably to COS Cells Overexpressing TM In this Example, the ability of Ang1-FD-Fc and Ang2-FD-Fc to bind to COS cells overexpressing TM was assessed. COS cells in 48-well plates were transfected with an expression vector containing TM, or with empty vector as a control. Two days after transfection, cells were incubated with 0, 0.16, 0.4, 1, 2.56, 6.4, 16, 40 or 100 nM of Ang1-FD-Fc (SEQ ID NO:5; residues 1-15 correspond to the signal peptide) or Ang2-FD-Fc (SEQ ID NO:6; residues 1-15 correspond to the signal peptide) in 200 µl binding buffer (PBS/10% calf serum) for 30 minutes at room temperature. After two PBS washes, cells were fixed in cold MeOH, followed by incubation with binding buffer containing alkaline phosphatase-conjugated secondary antibody (a 1:1000 dilution of alkaline phosphatase-conjugated goat anti-human Fc (Promega)) for 30 min. After two more PBS washes, 200 µl PNPP substrate (Sigma) was added. Reactions were stopped after 5 min by addition of 50 µl 3N NaOH, and the OD405 was taken as a measure of binding. Measurements were in quadruplicate. There was significant variability in these measurements, probably a consequence of avidity effects resulting from variable transfection efficiencies. Some nonspecific binding of Ang1-FD-Fc to the empty vector-transfected cells was observed at high concentrations, but was less than 20% of binding to cells expressing TM.

Specific binding, given in OD405 units, is defined as the difference between binding to TM-transfected COS cells and binding to COS cells transfected with empty vector. Both Ang1-FD-Fc and Ang2-FD-Fc, but not a control Fc protein, bound saturably to COS cells overexpressing TM (FIG. 1A), with apparent binding affinities of ~88 nM for Ang1-FD-Fc and ~8.3 nM for Ang2-FD-Fc.

The ability of an Ang2-FD-Fc triple mutant that does not bind to Tie2 (Barton, W. A. et al., 2005, Structure, 13:825-832; SEQ ID NO:7; residues 1-15 correspond to the signal peptide) to bind to COS cells overexpressing TM was assessed. In the Ang2-FD-Fc triple mutant, the mutated residues (F468A/Y474A/Y475A) are located at the Ang2/Tie2 interface (Barton, W. A., 2006, Nat. Struct. Mol. Biol. 13:524-532). In staining experiments (as described in Example 1), binding of the Ang2-FD-Fc triple mutant to COS cells overexpressing TM was not observed. This observation provides further support for the notion that residues at the angiopoietin/Tie2 binding interface are also required for binding to TM.

Example 3. BowAng1 and BowAng2 Bind Soluble Purified Extracellular Domain of TM

In this Example, the ability of the chimeric angiopoietins BowAng1 (SEQ ID NO:2) and BowAng2 (SEQ ID NO:4) to associate with the purified soluble extracellular domain of TM was assessed.

The soluble extracellular domain of human TM (R&D Systems) or the soluble extracellular domain of human Tie2 (produced at Regeneron; SEQ ID NO:9) at 100 nM were incubated with BowAng1 or BowAng2 at 100, 250 or 500 nM or with 500 nM human Fc control protein in binding buffer (0.15M NaCl, 20 mM Tris pH 7.5, 2 mM $CaCl_2$), 0.1% Triton X-100, 1 mg/ml BSA) on ice for 60 minutes. Following incubation, BowAng1, BowAng2 or human Fc were pulled down by incubation with 25 µl protein A/G beads (Santa Cruz Biotechnology) for 60 minutes. The beads were then washed with binding buffer and proteins were eluted by heating in SDS sample buffer and then resolved on an SDS gel. Co-precipitation of TM and Tie2 was assessed by western blot with an anti-TM monoclonal antibody (Santa Cruz Biotechnology (D-3), used at 1:500 dilution) or a monoclonal anti-Tie2 antibody (clone 33.1, Peters, K. G. et al., 1998, British Journal of Cancer, 77:51-56).

As a positive control, binding of BowAng1 and BowAng2 to the soluble extracellular domain of Tie2 was assessed. Both BowAng1 and BowAng2, but not a control protein (human Fc), associated with TM, with estimated EC50 values in the hundreds of nM (FIG. 1B). Consistent with the cell surface binding assay, BowAng2 bound to TM significantly more tightly than did BowAng1 (FIG. 1B). Since soluble TM is monomeric, this assay provides a measure of monomer-monomer interactions between TM and one fibrinogen-like domain of BowAng1 or BowAng2. Thus it is free of avidity effects inherent in the binding of dimeric forms of angiopoietins to cell surface TM (FIG. 1A), so it is not unexpected that lower apparent affinities are observed. The relatively low apparent affinity of angiopoietins for monomeric Tie2 observed here (estimated EC50 values in the hundreds of nM) is consistent with the previously reported avidity effects that are characteristic of angiopoietin-Tie2 binding (Davis, 2003, supra).

Co-precipitation experiments failed to provide evidence for the existence of the formation of complexes on the surface of cells that include both Tie2 and TM (data not shown).

Example 4. Soluble Tie2 Extracellular Domain Competes with TM for Binding to BowAng1 and BowAng2

In this Example, the ability of soluble Tie2 extracellular domain to compete with soluble TM extracellular domain for binding to BowAng1 and BowAng2 was assessed.

100 nM BowAng1 or BowAng2 was incubated with soluble extracellular domain of human TM (R&D Systems; 100 nM) in the absence or presence of excess (2 µM) soluble extracellular domain of human Tie2 (produced at Regeneron) in binding buffer (0.15M NaCl, 20 mM Tris pH 7.5, 2 mM CaCl$_2$), 0.1% Triton X-100, 1 mg/ml BSA) on ice for 60 minutes. Following incubation, BowAng1 or BowAng2 were pulled down by incubation with 25 µl protein A/G beads (Santa Cruz Biotechnology) for 60 minutes. The beads were then washed with binding buffer and proteins were eluted by heating in SDS sample buffer and then resolved on an SDS gel. Co-precipitation of TM and Tie2 was assessed by western blot with an anti-TM monoclonal antibody (Santa Cruz Biotechnology (D-3), used at 1:500 dilution) or a monoclonal anti-Tie2 antibody (clone 33.1 (Peters, supra).

Figure 1C:
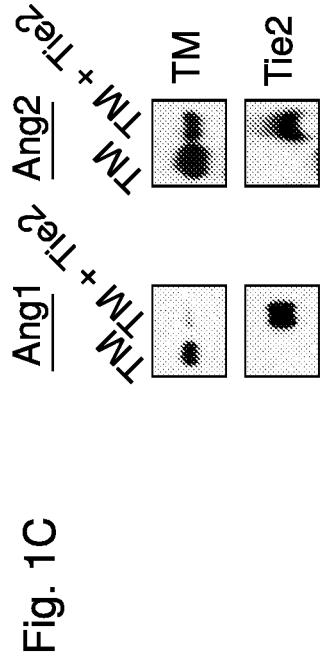
Figure 1A:
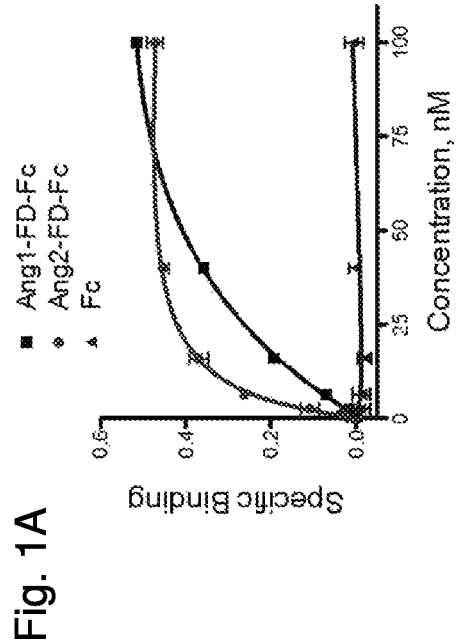

As shown in FIG. 1C, Tie2 competed with TM for binding to BowAng1 and BowAng2, suggesting that the binding sites on the angiopoietins for TM and Tie2 do overlap. However, Tie2 was less effective at competing with TM for binding to BowAng2, consistent with the observation that BowAng2 appears to bind TM more tightly than does BowAng1, while binding less tightly than BowAng1 to Tie2 in this solution binding assay (FIG. 1B).

Example 5. Native Ang1 and Ang2 Inhibit APC and TAFI Formation in Cultured HUVECs In this Example, the ability of angiopoietins to modulate the thrombin/TM dependent activation of protein C and TAFI was assessed. Addition of protein C or TAFI to cultured endothelial cells in the presence of thrombin results in cleavage of these substrates in a TM-dependent fashion (Hackeng, T. M. et al., 1996, The Biochemical journal. 319 (Pt 2):399-405; Hockin, M. F., et al., 1997, Arteriosclerosis, thrombosis, and vascular biology. 1997; 17:2765-2775; Slungaard, A. et al., 2003, Blood. 102:146-151). Several previous reports have used cultured endothelial cells to assess the effects of various proteins (e.g., the platelet α-granule protein platelet factor 4 (PF4)) on the activity of the thrombin/TM complex (Slungaard, supra).

APC formation on HUVEC monolayers was assessed using a modified version of a previously described method (Slungaard, supra). 50,000 HUVECs (VEC Technologies) were plated in 48-well plates in 200 µl of MCDB131 complete medium. The next day the cells were washed three times with reaction buffer (HBSS+10 mM HEPES pH 7.4+1 mg/ml BSA) and then incubated for 60 min at 37° C. with 100 µl of reaction buffer containing 0.2 µM protein C (Enzyme Research Labs), 0.1 U/ml thrombin (Sigma) and native human Ang1 (R&D Systems), native human Ang2 (R&D Systems), human PF4 (R&D Systems) or a control Fc-containing protein at 1, 10, 50, 100, 500 or 1000 nM. Following incubation, cell supernatants (90 µl of buffer from each well) were transferred to a 96 well plate and incubated with the thrombin inhibitor hirudin (Sigma) at 25 U/ml for 10 minutes at 37° C. The chromogenic APC substrate S-2366 (Chromogenix) was then added at 0.2 mM and cleavage of S-2366 was followed by monitoring the change in OD 405 nm. The OD 405 nm at ~10 minutes after S-2366 addition (the OD 405 nm was still increasing linearly at this time point) was used to assess the relative levels of TM-dependent APC formation in each sample (after subtracting the value observed when the procedure was carried out with no HUVECs in the wells).

Figures 2A, 2B, 2C, 2D, 2E:
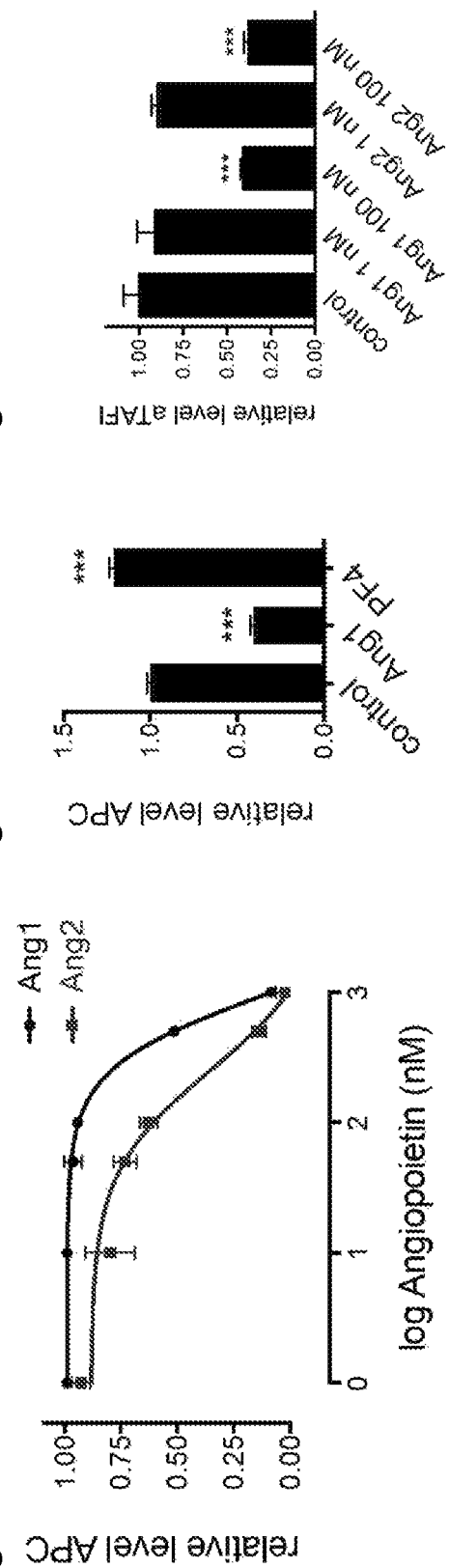
FIGS. 2A, 2B, 2C, 2D and 2E show that Ang1 and Ang2 inhibit TM-dependent formation of APC and aTAFI.

The graph in FIG. 2A depicts the relative amounts of APC formation (compared to APC formation in the presence of the control protein) as a function of angiopoietin concentration. The error bars represent the SD, n=3. Both Ang1 and Ang2 substantially inhibited APC formation (relative to the amount generated in the presence of 1 µM of a control protein), with IC$_{50}$ values in the hundreds of nM (FIG. 2A). Consistent with its higher affinity for TM, Ang2 was a more potent inhibitor of APC production than was Ang1 (FIG. 2A).

As an additional control for the specificity of the assay, the effect of PF4 on APC formation in HUVECs was assessed. HUVECs were incubated with protein C and thrombin plus either a control protein (0.5 µM), native Ang1 (0.5 µM) or PF4 (10 µg/ml, ~1.3 µM) for 60 minutes and cell supernatants were then assayed for APC levels. The graph in FIG. 2B depicts the relative amounts of APC generated (the amount of APC generated in the presence of the control protein was assigned a value of 1.0). The error bars represent the SD, n=3. Relative levels of APC in the Ang1 and the PF4 treatment groups were significantly different from the control group (***, P<0.001, one-way ANOVA with Tukey's multiple comparisons test). In contrast to angiopoietins, addition of PF4 to the HUVECs modestly increased APC formation (FIG. 2B), as demonstrated previously (Slungaard, supra).

The ability of angiopoietins to affect aTAFI formation in HUVECs was assessed. 50,000 HUVECs (VEC Technologies) were plated in 48-well plates in 200 µl of MCDB131 complete medium. The next day the cells were washed three times with reaction buffer (HBSS+10 mM HEPES pH 7.4+1 mg/ml BSA) and then incubated at 37° C. for 60 minutes with 100 µl of reaction buffer containing 0.2 µM TAFI (Enzyme Research Labs), 1 U/ml thrombin, and native human Ang1 (1 nM or 100 nM), native human Ang2 (1 nM or 100 nM) ora control Fc-containing protein (1 µM). Following incubation, cell supernatants were used to measure aTAFI activity using the fluorogenic ACTIFLUOR TAFIa Activity Assay (American Diagnostica).

The graph in FIG. 2C depicts the relative amounts of aTAFI generated (the amount of aTAFI generated in the presence of the control protein was assigned a value of 1.0). The error bars represent the SD, n=3. Relative levels of aTAFI in the Ang1 100 nM and the Ang2 100 nM treatment groups were significantly different from the control group (***, P<0.001, one-way ANOVA with Tukey's multiple comparisons test). Similar to their effect on formation of APC, native Ang1 and Ang2 at 100 nM significantly inhibited aTAFI formation in HUVECs (FIG. 2C).

These experiments indicate that in addition to binding TM, native Ang1 and Ang2 inhibit TM function in endothelial cells.

Example 6. Ang1 and Ang2 Inhibit Both APC and aTAFI Formation in COS Cells Overexpressing TM but Lacking Tie2 Expression (Inhibition does not Require Tie2)

In this Example, the ability of Ang1 and Ang2 to inhibit APC and aTAFI formation in COS cells overexpressing TM but lacking Tie2 expression was assessed.

COS7 cells transfected with expression vectors for TM or control empty vector were seeded, one day after transfection, into 48 well plates (80,000/well). The next day, cells were washed three times with reaction buffer (HBSS+10 mM HEPES+1 mg/ml BSA) and then incubated with 100 µl of reaction buffer containing 1, 3, 9, 27, 81, 243, or 729 nM of native human Ang1 or Ang2 for 30 minutes at 4° C. 0.2 µM protein C and 0.1 U/ml thrombin were then added and incubated for 60 minutes at 37° C. Following incubation, the reaction was stopped with hirudin and APC levels were determined, as above.

Following incubation, 90 µl of buffer from each well was transferred to a 96 well plate and incubated with the thrombin inhibitor hirudin (Sigma) at 25 U/ml for 10 minutes at 37° C. The chromogenic APC substrate S-2366 (Chromogenix) was then added at 0.2 mM and cleavage of S-2366 was followed by monitoring the change in OD 405 nm. The OD 405 nm at ~10 minutes after S-2366 addition (the OD 405 nm was still increasing linearly at this time point) was used to assess the relative levels of TM-dependent APC formation in each sample (after subtracting the value observed when the procedure was carried out with no HUVECs in the wells). The graph in FIG. 2D depicts relative APC formation as a function of angiopoietin concentration (the amount formed in the absence of angiopoietin was assigned a value of 1.0)

The ability of angiopoietins to affect aTAFI formation in COS cells was assessed. COS cells transfected with expression vectors for TM or control empty vector in 10 cm dishes were rinsed in PBS, collected using a spatula, disaggregated by trituration, and pelleted. Cells were resuspended in reaction buffer (HBSS+10 mM HEPES pH7.4+1 mg/ml BSA, 80,000 cells/reaction) and incubated with 72 µl of reaction buffer containing various concentrations of native human Ang1 or Ang2 (1, 3, 9, 27, 81, 243, or 729 nM) for 30 minutes at 4° C. Following this, 0.2 µM TAFI and 1 U/ml thrombin were added in a final volume of 80 µl and incubated for 30 minutes at 22° C. Cells were then pelleted and 75 µl of the supernatants were transferred to a 96 well plate. 25 µl of 2 mM 5,5'-dithiobis-(2-nitrobenzoic acid) (Sigma) and 50 µl of a thiol-releasing TAFI substrate (R2 reagent, Pefakit TAFI, Pentapharm) were then added, and the OD 405 nm at 10 minutes was used to determine TAFI activity. The graph in FIG. 2E depicts aTAFI formation relative to the amount generated in the absence of angiopoietin.

In COS cells overexpressing TM, but lacking Tie2 expression, angiopoietins significantly inhibited both APC and aTAFI formation, indicating that the inhibition does not require Tie2 (FIGS. 2D and 2E). In contrast to their effect in HUVECs, angiopoietin-mediated inhibition in COS cells was observed even at low nM concentrations, presumably reflecting enhanced, avidity-driven angiopoietin binding to overexpressed TM. A possible explanation for this observation is that in HUVECs, the endothelial Protein C receptor (EPCR) makes blockade of APC formation more difficult than in COS cells. EPCR is expressed at high levels in HUVECs and binds Protein C with high affinity (40), promoting delivery of protein C to the thrombin/TM complex, thus amplifying its activity (41). In this context, it is interesting to note that, in contrast to HUVECs, EPCR is expressed at low levels in microvasculature (Laszik Z., et al., 1997, Circulation. 96:3633-3640).

Example 7. Inhibition of APC Formation by Ang1 is Independent of Tie2

In this Example, the effect of knocking down Tie2 expression on Ang1-dependent inhibition of APC-formation in HUVECs was assessed. HUVECs were infected with adenoviruses (~30 pfu/cell) encoding either a non-silencing control shRNA or a Tie2 specific shRNA as described (Daly, C. et al., 2004, Genes & Development. 18:1060-1071.

Figure 3A:
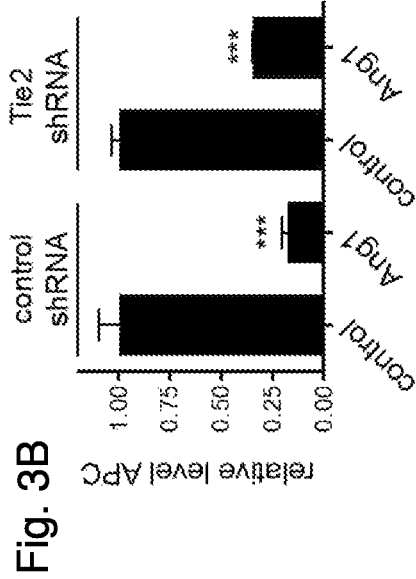
FIGS. 3A and 3B show that inhibition of APC formation by Ang1 is independent of Tie2.
Figure 3B:
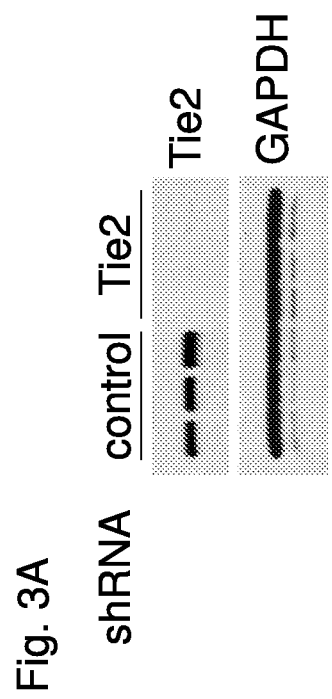

The sequence of the Tie2 shRNA was: 5'-TGAAGTAC-CTGATATTCTA-3' (SEQ ID NO:8) (nucleotides 946-964 in the human Tie2 (TEK) cDNA, NM_000459). At 3 days after infection, cells were either lysed for Western blot to demonstrate Tie2 knockdown (FIG. 3A) or used to test the effect of native Ang1 on APC formation in the presence of protein C and thrombin (FIG. 3B). The APC assay was done as described in Example 5 above (except that thrombin was present at 1 U/ml), in the presence of 1 µM control protein or Ang1. Western blot for Tie2 was performed with the monoclonal antibody clone 33.1 (Peters, supra).

The graph in FIG. 3B depicts the relative amounts of APC generated in the presence of 1 µM control protein or native Ang1 (the amount of APC generated in the presence of the control protein was assigned a value of 1.0). The error bars represent the SD, n=3. Ang1 significantly inhibited APC formation in cells treated with control shRNA or Tie2 shRNA (***, P<0.001, one-way ANOVA with Tukey's multiple comparisons test).

Despite almost complete inhibition of Tie2 expression by the shRNA (FIG. 3A), Ang1 was still capable of inhibiting APC formation (FIG. 3B), indicating that Tie2 is not required for this effect.

Example 8. Ang1 and Ang2 Inhibit Binding of Thrombin to TM

In this Example, the ability of Ang1 and Ang2 to inhibit binding of thrombin to TM was assessed in vitro. Soluble TM extracellular domain (with a 6-His tag) at 100 nM was incubated with 5 nM thrombin (Sigma) in the presence of 1 µM of an Fc-containing control protein or 0.25, 0.5 or 1.0 µM native Ang1 (FIG. 4A) or native Ang2 (FIG. 4B) in binding buffer (0.15M NaCl, 20 mM Tris pH 7.5, 0.1% Triton X-100, 2 mM $CaCl_2$), 1 mg/ml BSA) for 60 minutes on ice. TM was then pulled down by incubation for 60 minutes with 20 µl Ni-NTA beads (Thermo Scientific). Beads were then washed with binding buffer and bound proteins were eluted by heating in SDS sample buffer. Western blots were then performed to assess pull-down of TM (monoclonal antibody D-3 from Santa Cruz Biotechnology) and co-precipitation of thrombin (goat polyclonal antibody from R&D Systems).

Figure 4A:
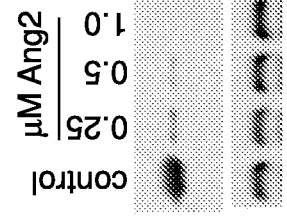
FIGS. 4A and 4B show that Ang1 and Ang2 inhibit binding of thrombin to TM.
Figure 4B:
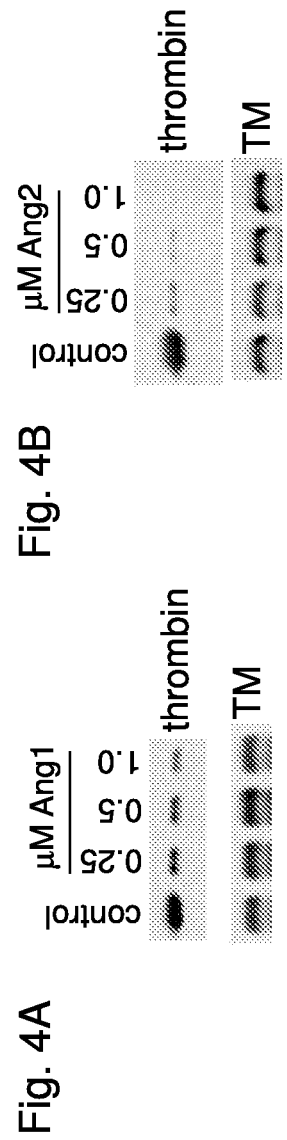

Increasing concentrations of native Ang1 or Ang2 progressively inhibited the association of thrombin with soluble TM in vitro, with Ang2 having a more potent effect (FIG. 4A, 4B). This result suggests that angiopoietins can inhibit formation of a stable complex of thrombin with TM, and that this is one mechanism by which angiopoietins interfere with generation of APC and aTAFI.

Example 9. Ang1 is Present in Mouse Platelets

In this Example, the presence of Ang1 in mouse platelets was assessed. It has been reported that human platelets contain Ang1 and release it upon stimulation with thrombin in vitro (Li, J. J. et al., 2001, Thromb. Haemost. 85:204-206).

All mouse experiments were approved by Regeneron's Institutional Animal Care and Use Committee. Blood was collected from C57Bl/6 mice by cardiac puncture and expelled into tubes containing EDTA and immediately mixed. Blood was then centrifuged at 300×g for 10 minutes. The supernatant (platelet-rich plasma) was collected and spun at 2,000×g for 10 minutes and the pellet was then resuspended directly in SDS sample buffer and heated. Aliquots of platelet lysate representing ~1.6×10$^6$ platelets were run on SDS gels along with the indicated amounts (ng) of mouse PF4, human Ang1 or human Ang2 to allow estimation of the levels of these proteins in the platelet lysate. Ang1 was detected with a rabbit polyclonal antibody that recognizes both mouse and human Ang1 (mouse and human Ang1 proteins are 97% identical). Ang2 was detected with a goat polyclonal antibody raised against a peptide that is identical in the human and mouse proteins.

Aliquots of platelet lysate were then used in western blots, probing for PF4 (goat polyclonal from R&D Systems raised against mouse PF4, used at 1:5000 dilution), Ang1 (rabbit polyclonal generated at QCB for Regeneron, used at 1 µg/ml) or Ang2 (goat polyclonal (C-19) from Santa Cruz Biotechnology, used at 1:200 dilution). The Ang1 and Ang2 antibodies recognize both the mouse and human proteins.

Figure 5A:
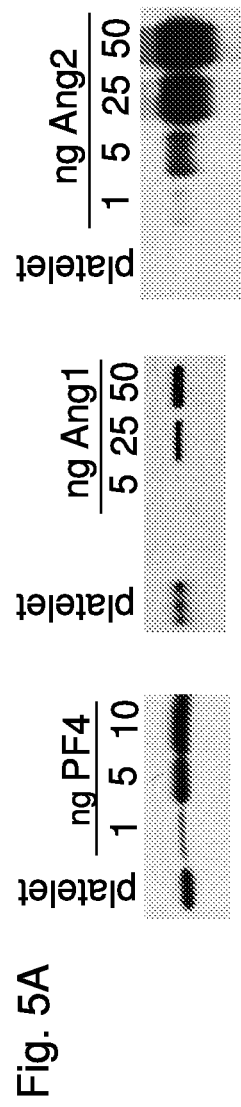

As shown in FIG. 5A, Ang1 protein was detected in mouse platelets at levels (~30 ng/$10^6$ platelets) similar to those reported in human platelets (~55 ng/$10^6$ platelets) (46). As a positive control, the presence of PF4 was detected in platelet lysate at ~3 ng/$10^6$ platelets, similar to the estimated level of PF4 in human platelets (~12 ng/$10^6$ platelets) (Peterson J. E., et al., 2010, American journal of hematology, 85:487-493). In contrast, Ang2 was not detected in mouse platelets (FIG. 5A). The polyclonal antibody used to detect Ang2 was raised against a peptide that is identical in human/mouse Ang2 and this antibody readily detects Ang2 in mouse tissue lysates by western blot. While Ang2 is not observed in platelets, it is present in endothelial cell Weibel-Palade bodies (WPB) and is released upon stimulation with thrombin in vitro (Fiedler, U. et al, 2004, Blood, 103:4150-4156), suggesting the possibility that Ang2 is released from activated endothelial cells at sites of vessel injury. Ang1 is present in mouse platelets (FIG. 5A) but Ang2 is not detected in mouse platelets (Ang2 has been shown in art to be found in endothelial cell Weibel-Palade bodies).

Example 10. Ang1 is 100× Higher in Serum than in Plasma

In this Example, the level of Ang1 was measured in mouse serum and mouse plasma.

For serum preparation, blood was collected by cardiac puncture and expelled into serum separator tubes (BD Biosciences). Following a 30 minute incubation to allow for blood clotting, samples were centrifuged at 2,000×g for 10 minutes and the serum layer was collected and stored at −80° C.

For plasma preparation, blood was collected by cardiac puncture, expelled into EDTA tubes (BD Biosciences), mixed and then centrifuged at 2,000×g at 4° C. for 10 minutes. The supernatant (platelet-poor plasma) was collected and centrifuged again at 2,000×g for 10 minutes. The plasma supernatant was collected and either used immediately or stored in aliquots at −80° C.

Blood was collected from C57BL/6 mice by cardiac puncture and used to prepare either plasma or serum. Ang1 and PF4 levels were then determined by ELISA.

Ang1 ELISA: 96 well ELISA plates (Corning) were coated overnight at 4° C. with 10 µg/ml of His-tagged Tie2 extracellular domain. Wells were washed 3 times with PBS+0.05% Tween 20 (PBST) and blocked for 2 hours at RT with PBS+3% BSA. Wells were washed again and incubated for 1 hour with 100 µl of protein standard (recombinant human Ang1 from R&D Systems) or plasma/serum samples diluted in PBST+3% BSA. Plasma samples were diluted 1:5, serum samples were diluted 1:20. Wells were then washed and incubated at RT for 1 hour with 100 µl of biotinylated goat anti-Ang1 antibody (R&D Systems, catalog number BAF923) at 0.2 µg/ml. Wells were then washed and incubated in 100 µl of streptavidin-HRP (R&D Systems) at 1:200 dilution for 20 minutes at RT. Wells were then washed and incubated for 20 minutes at RT with 100 µl of substrate solution (R&D Systems, catalog number DY999) protected from light. 50 µl of 1M sulfuric acid was added to stop the reactions and OD values were read at 450 nm with subtraction at 540 nm.

PF4 ELISA was performed according to the protocol outlined in the mouse CXCL4/PF4 DuoSet (R&D Systems, catalog number DY595). Plasma samples were diluted 1:10 or 1:50 and serum samples were diluted 1:2000.

Figure 5B:
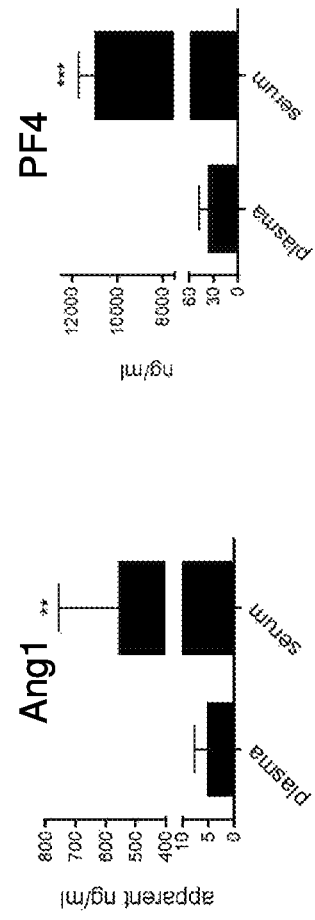

Ang1 levels are given as apparent concentrations since the standard curve used to estimate Ang1 concentration was generated with human Ang1 protein. Bars represent the mean and SD, n=4. Both Ang1 and PF4 levels were significantly higher in serum (, $P<0.01$; *, $P<0.001$, t-test). Consistent with Ang1 release from platelets upon degranulation ex vivo, Ang1 levels were ~100-fold higher in serum than in plasma (FIG. 5B). Similarly, PF4 levels were hundreds of fold higher in serum, providing a positive control (FIG. 5B). Due to the lack of availability of a reliable mouse Ang2 ELISA, we were not able to compare Ang2 levels in mouse serum versus plasma. However, consistent with our data showing the absence of Ang2 in platelets, Ang2 levels in plasma and serum from healthy volunteers are similar (<5 ng/ml) (Goede, V., et al., 2010 British Journal of Cancer, 103:1407-1414; Wang, X., et al., 2014, Translational Oncology, 7:188-195).

Example 11: Ang1 is Released from Activated Platelets In Vivo

To determine whether Ang1 is released from activated platelets in vivo, plasma levels of Ang1 (and PF4 as a positive control) were measured 10 minutes after intravenous administration of thrombin to mice.

C57BL/6 mice were injected into the tail vein with PBS or 10 units of thrombin (Sigma) in a volume of 100 µl. At 10 minutes after injection, blood was drawn by cardiac puncture and plasma was prepared for use in Ang1 and PF4 ELISAs as in Example 10. Plasma levels of Ang1 and PF4 were determined by ELISA. Bars represent the mean and SD (n=9 for PBS, n=8 for thrombin). The levels of both Ang1 and PF4 were significantly higher in the thrombin treated samples (, $P<0.01$; *, $P<0.001$, t-test). Any bloods that were difficult to draw were discarded and plasma samples in which the Ang1 level was >30 ng/ml were not used in the analysis, as these samples appeared to be outliers and likely had some degree of platelet activation and Ang1 release ex vivo.

As shown in FIG. 5C, plasma levels of both Ang1 and PF4 were significantly higher following acute thrombin treatment, consistent with release of both of these factors from activated platelets. Ang1 plasma level is higher following acute thrombin treatment (consistent with Ang1 being released from activated platelets) (FIG. 5C).

Example 12: Ang1 is Released from Platelets in Response to Blood Vessel Injury

To assess whether Ang1 is released from platelets in response to blood vessel injury, Ang1 levels were measured in plasma prepared from blood collected at the site of tail nicks in mice.

Blood was collected from C57BL/6 mice either by cardiac puncture (systemic) (see Example 9) or by tail nick. For tail nick experiments to assess the levels of Ang1 in wound blood, C57BL/6 mice were placed under a heating lamp for approximately 5 min. Mice were then placed in a restrainer and the distal 2 to 4 mm of tail was severed with a single diagonal cut. Blood was collected into heparinized capillary tubes for an initial period of 30 seconds and discarded. Blood was then collected into a second heparinized capillary tube until the tube was full (this took 2-5 minutes). A disposable Pasteur pipette was used to expel the blood into a microfuge tube containing EDTA. Plasma was then prepared as described above. For this experiment, the samples used to assess systemic plasma Ang1 levels were collected by cardiac puncture of naïve animals. To mimic the procedure for preparation of plasma from wound blood, the blood was stored in heparinized capillary tubes for 4-5 min before being expelled into a microfuge tube containing EDTA. To ensure that the higher levels of Ang1 in the tail nick samples did not simply reflect differences in the plasma preparation procedures, the cardiac puncture blood samples were incubated in heparinized capillary tubes for 4-5 minutes before proceeding with plasma isolation to mimic the procedure for the tail nick samples. Plasma was prepared and Ang1 and PF4 levels were determined by ELISA. Plasma was prepared and Ang1 and PF4 levels were determined by ELISA as in Example 10. Bars represent the mean and SD (n=9 for systemic samples, n=10 for tail nick samples). The levels of both Ang1 and PF4 were significantly higher in the tail nick samples (***, P<0.001, t-test).

Both Ang1 and PF4 levels were significantly higher in plasma prepared from tail nick blood than in plasma prepared from systemic blood (collected via cardiac puncture) (FIG. 5D), suggesting release of Ang1 from platelets at the site of injury. Ang1 level was higher in plasma prepared from tail nick blood than in plasma prepared from systemic blood, suggesting release of Ang1 from platelets at the site of injury (FIG. 5D).

Example 13. Intravenous Administration of BowAng1 and BowAng2 to Mice Promotes a Rapid Increase in Circulating Thrombin/Antithrombin Level and Fibrin Deposition in Lung In this Example, the effect of BowAng1 and BowAng2 on circulating thrombin/antithrombin level and on fibrin deposition in lung was assessed.

At 20 minutes following intravenous injection of 6 mg/kg of Fc control, BowAng1 or BowAng2, lungs were harvested. Lungs were homogenized in ice-cold PBS containing cOmplete™ protease inhibitor cocktail (with EDTA) plus 10 units/ml heparin. Following overnight incubation at 4° C., lysates were spun for 10 minutes in a microcentrifuge. The pellets were resuspended in 3M urea and incubated at 37° C. for 2 hours to extract cross-linked fibrin. Samples were then vortexed and spun for 10 minutes in a microcentrifuge. Pellets were resuspended in SDS-PAGE sample buffer and incubated at 65° C. for 90 minutes. The amount of fibrin in the samples was determined by Western blot using a monoclonal anti-fibrin antibody from American Diagnostica (FIG. 6A).

At 20 minutes following intravenous injection of Fc control, BowAng1 (7.5 mg/kg) or BowAng2 (4 mg/kg), the levels of thrombin/antithrombin III complex in plasma were measured using a sandwich enzyme immunoassay kit (Enzygnost® TAT micro, Dade Behring) (FIG. 6B).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of treating, preventing or ameliorating at least one symptom, indication or complication of a blood coagulation disorder, comprising administering to a subject in need thereof a pharmaceutical composition comprising a therapeutically effective amount of a fusion protein comprising angiopoietin-1 or a portion thereof fused to an immunoglobulin Fc fragment, and a pharmaceutically acceptable carrier, wherein the pharmaceutical composition stimulates blood coagulation in the subject.

2. The method of claim 1, wherein the blood coagulation disorder is selected from the group consisting of inborn platelet pathologies, platelet disorders caused by insufficient production, platelet disorders caused by destruction by the immune system, coagulation factor disorders, and disorders associated with warfarin treatment, aspirin treatment, surgery, or injury.

3. The method of claim 1, wherein the angiopoietin protein binds purified soluble extracellular domain of thrombomodulin with an $EC_{50}$ value of less than 100 nM.

4. The method of claim 1, wherein the angiopoietin protein is administered intravenously.

5. The method of claim 1, wherein the angiopoietin protein is administered subcutaneously.

6. The method of claim 1, wherein the fusion protein comprises at least one fibrinogen-like domain of angiopoietin-1 fused to an Fc fragment.

7. The method of claim 6, wherein the fusion protein comprises:

i) a first fibrinogen-like domain of angiopoietin-1 fused at the C-terminal end to the N-terminal end of an Fc fragment, and ii) the Fc fragment fused at the C-terminal end to the N-terminal end of a second fibrinogen-like domain of angiopoietin-1.

8. The method of claim 7, wherein the fusion protein is AngF1-Fc-F1.

9. The method of claim 8, wherein the fusion protein comprises the amino acid sequence of SEQ ID NO: 2.

10. The method of claim 2, wherein the blood coagulation disorder is an inborn platelet pathology selected from the group consisting of: thrombasthenia of Glanzmann and Naegeli, Bernard-Soulier syndrome, gray platelet syndrome, delta storage pool deficiency, and Von Willebrand disease.

11. The method of claim 2, wherein the blood coagulation disorder is a platelet disorder selected from the group consisting of: myelodysplastic syndrome and immune thrombocytopenic purpura.

12. The method of claim 2, wherein the blood coagulation disorder is a coagulation factor disorder selected from the group consisting of: hemophilia, deficiency of Vitamin K, a Factor XII mutation, thrombocytopenia, uremia, and congenital afibrinogenemia.

13. The method of claim 12, wherein the hemophilia is selected from the group consisting of hemophilia A, hemophilia B, and hemophilia C.

14. The method of claim 2, wherein the blood coagulation disorder is a liver failure disorder selected from the group consisting of acute liver failure, chronic liver failure, early liver failure, and end-stage liver failure.

15. The method of claim 2, wherein the blood coagulation disorder is associated with warfarin treatment, aspirin treatment, surgery, or injury.

* * * * *